(12) United States Patent
Aqad et al.

(10) Patent No.: US 11,613,519 B2
(45) Date of Patent: Mar. 28, 2023

(54) PHOTOACID-GENERATING MONOMER, POLYMER DERIVED THEREFROM, PHOTORESIST COMPOSITION INCLUDING THE POLYMER, AND METHOD OF FORMING A PHOTORESIST RELIEF IMAGE USING THE PHOTORESIST COMPOSITION

(71) Applicant: Rohm and Haas Electronic Materials LLC, Marlborough, MA (US)

(72) Inventors: Emad Aqad, Northborough, MA (US); James W. Thackeray, Braintree, MA (US); James F. Cameron, Brookline, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 0 days.

(21) Appl. No.: 15/131,135

(22) Filed: Apr. 18, 2016

(65) Prior Publication Data

US 2017/0248844 A1 Aug. 31, 2017

Related U.S. Application Data

(63) Continuation-in-part of application No. 15/055,911, filed on Feb. 29, 2016, now abandoned.

(51) Int. Cl.
| | |
|---|---|
| C07C 309/17 | (2006.01) |
| C07C 309/06 | (2006.01) |
| C07C 309/07 | (2006.01) |
| C07C 309/12 | (2006.01) |
| C07C 309/20 | (2006.01) |
| C07C 309/23 | (2006.01) |
| C07C 309/42 | (2006.01) |
| G03F 7/004 | (2006.01) |
| C08F 224/00 | (2006.01) |
| G03F 7/039 | (2006.01) |
| C07C 303/32 | (2006.01) |

(52) U.S. Cl.
CPC .......... *C07C 309/06* (2013.01); *C07C 303/32* (2013.01); *C07C 309/07* (2013.01); *C07C 309/12* (2013.01); *C07C 309/17* (2013.01); *C07C 309/20* (2013.01); *C07C 309/23* (2013.01); *C07C 309/42* (2013.01); *C08F 224/00* (2013.01); *G03F 7/0045* (2013.01); *G03F 7/0397* (2013.01)

(58) Field of Classification Search
CPC ................ C07C 309/06; C07C 309/07; C07C 309/12; C07C 309/20; C07C 309/23; C07C 309/42; C07C 303/32; G03F 7/0045; G03F 7/0392; G03F 7/30
USPC ...... 526/287; 562/100, 109, 113, 36, 41, 42, 562/102, 105, 106; 560/147, 149, 153, 560/205, 219, 220, 221, 223, 225, 226, 560/227, 228, 229, 252, 254, 255, 256
See application file for complete search history.

(56) References Cited

U.S. PATENT DOCUMENTS

| | | | |
|---|---|---|---|
| 2,760,863 A | 8/1956 | Plambeck, Jr. | |
| 2,850,445 A | 9/1958 | Oster | |
| 2,875,047 A | 2/1959 | Oster | |
| 3,097,096 A | 7/1963 | Oster | |
| 3,427,161 A | 2/1969 | Laridon et al. | |
| 3,479,185 A | 11/1969 | Chambers, Jr. | |
| 3,549,367 A | 12/1970 | Chang et al. | |
| 4,343,885 A | 8/1982 | Reardon, Jr. | |
| 4,442,197 A | 4/1984 | Crivello et al. | |
| 4,603,101 A | 7/1986 | Crivello | |
| 4,624,912 A | 11/1986 | Zweifel et al. | |
| 7,569,324 B2 * | 8/2009 | Kobayashi | C07C 309/00 430/270.1 |
| 7,569,326 B2 * | 8/2009 | Ohsawa | C08F 20/22 430/270.1 |
| 7,838,199 B2 | 11/2010 | Thackeray et al. | |
| 8,057,985 B2 * | 11/2011 | Ohashi | C07C 309/12 430/270.1 |
| 8,283,106 B2 * | 10/2012 | Maeda | C07C 309/12 430/270.1 |
| 8,288,076 B2 | 10/2012 | Masunaga et al. | |
| 8,431,325 B2 | 4/2013 | Hashimoto et al. | |
| 8,507,176 B2 | 8/2013 | Thackeray et al. | |
| 8,716,518 B2 | 5/2014 | Coley et al. | |
| 8,900,792 B2 | 12/2014 | Thackeray et al. | |
| 8,907,122 B2 | 12/2014 | Coley et al. | |
| 8,945,814 B2 | 2/2015 | Cameron et al. | |
| 9,156,785 B2 * | 10/2015 | Aqad | C07C 63/72 |
| 9,182,669 B2 | 11/2015 | Ongayi et al. | |
| 2010/0055608 A1 * | 3/2010 | Ohashi | C07C 309/12 430/270.1 |
| 2010/0063232 A1 | 3/2010 | Nagai et al. | |
| 2011/0189609 A1 | 8/2011 | Kawabata et al. | |

(Continued)

FOREIGN PATENT DOCUMENTS

| | | |
|---|---|---|
| JP | 2013082894 A | 5/2013 |
| SG | 177080 A1 | 1/2012 |

*Primary Examiner* — John S Chu
(74) *Attorney, Agent, or Firm* — Cantor Colburn LLP

(57) ABSTRACT

A monomer has the structure

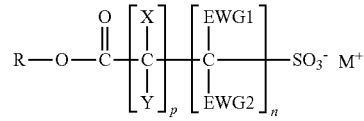

wherein R is an organic group comprising a polymerizable carbon-carbon double bond or carbon-carbon triple bond; X and Y are independently at each occurrence hydrogen or a non-hydrogen substituent; EWG1 and EWG2 are independently at each occurrence an electron-withdrawing group; p is 0, 1, 2, 3, or 4; n is 1, 2, 3, or 4; and $M^+$ is an organic cation. A polymer prepared from monomer is useful as a component of a photoresist composition.

15 Claims, 2 Drawing Sheets

(56) References Cited

U.S. PATENT DOCUMENTS

| | | |
|---|---|---|
| 2011/0269070 A1 | 11/2011 | Aqad et al. |
| 2012/0171616 A1 | 7/2012 | Thackeray et al. |
| 2013/0143163 A1* | 6/2013 | Hatakeyama ........ C09D 145/00 430/296 |
| 2013/0252170 A1 | 9/2013 | Han et al. |
| 2014/0080062 A1 | 3/2014 | Thackeray et al. |
| 2014/0186767 A1 | 7/2014 | Thackeray et al. |
| 2014/0212797 A1 | 7/2014 | Kawabata et al. |
| 2015/0093709 A1 | 4/2015 | Labeaume |
| 2015/0177613 A1 | 6/2015 | Jain et al. |
| 2015/0177615 A1 | 6/2015 | Jain et al. |

\* cited by examiner

PHOTOACID-GENERATING MONOMER, POLYMER DERIVED THEREFROM, PHOTORESIST COMPOSITION INCLUDING THE POLYMER, AND METHOD OF FORMING A PHOTORESIST RELIEF IMAGE USING THE PHOTORESIST COMPOSITION

CROSS REFERENCE TO RELATED APPLICATIONS

This application claims the benefit of U.S. Nonprovisional application Ser. No. 15/055,911, filed 29 Feb. 2016, the contents of which are incorporated herein in their entirety.

FIELD

The present invention relates to a monomer with a photoacid-generating group, a polymer formed from the monomer, a photoresist composition comprising the polymer, and a method of forming a photoresist relief image with the photoresist composition.

INTRODUCTION

Advance lithographic techniques such as electron beam and Extreme Ultraviolet (EUV) lithographies are being used for the formation of fine patterns. Further shrinking of pattern size to 25 nanometers and less requires, in addition to other process and tool related requirements, the development of highly resolving chemical amplified chemically amplified photoresist compositions. The use of slow diffusion photoacid generator (PAG) additives was proved to be critical for the improvement in resolution and pattern quality. Slow acid diffusion in a chemically amplified photoresist composition was achieved by attaching the acidic unit to one or more bulky and polar substituents. However, increasing PAG volume has the disadvantage of lowering PAG solubility in typical photoresist composition solvents. As a consequence, voluminous PAGs are subject to segregation or inhomogeneous distribution in the photoresist film matrix. In addition, reduced PAG solubility narrows photoresist composition formulation space and limits the amount of PAG that can be loaded in chemically amplified photoresist compositions. Moreover, low PAG solubility is associated with the formation of defects during and after lithographic processing.

An alternative approach for achieving slow PAG diffusion is realized by attaching the photoacid generator to a photoresist polymer backbone. Among the advantages of Polymer-Bound-PAG (PBP) are exceptionally slow acid diffusion, homogenous PAG distribution, and higher PAG loading capability. Polymerizable PAGs and corresponding polymers are described, for example, in U.S. Pat. Nos. 7,838,199 B2 and 8,507,176 B2 and 8,900,792 B2 to Thackeray et al., U.S. Pat. Nos. 8,716,518 B2 and 8,907,122 B2 to Coley et al., U.S. Pat. No. 8,945,814 B2 to Cameron et al., and U.S. Pat. No. 9,182,669 B2 to Ongayi et al., as well as U.S. Patent Application Publication Nos. US 2014/0080062A1 and US 2014/0186767 A1 of Thackeray et al., US 2015/0093709 A1 of LaBeaume, and US 2015/0177613 A1 and US 2015/0177615 A1 of Jain et al.

There remains a need for polymerizable PAGs and corresponding polymers and photoresist compositions that exhibit resolution of features on the scale of 20 to 26 nanometers or smaller, while providing low unexposed film thickness loss, and acceptable photospeed, pattern collapse margin, exposure latitude, and line width roughness.

SUMMARY

One embodiment is a monomer having the structure

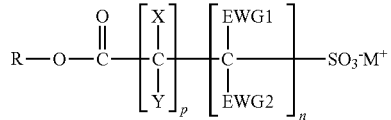

wherein R is an organic group comprising a polymerizable carbon-carbon double bond or carbon-carbon triple bond; X and Y are independently at each occurrence hydrogen or a non-hydrogen substituent; EWG1 and EWG2 are independently at each occurrence an electron-withdrawing group; p is 0, 1, 2, 3, or 4, provided that p is 1, 2, 3, or 4 when EWG1 and EWG2 are each independently fluoro, trifluoromethyl, or pentafluoroethyl; n is 1, 2, 3, or 4; and $M^+$ is an organic cation.

Another embodiment is a polymer comprising repeat units derived from the monomer.

Another embodiment is a photoresist composition comprising the polymer.

Another embodiment is a method of forming a photoresist relief image, comprising: (a) applying a layer of the photoresist composition on a substrate to form a photoresist layer; (b) pattern-wise exposing the photoresist layer to activating radiation to form an exposed photoresist layer; and (c) developing the exposed photoresist layer to provide a photoresist relief image.

These and other embodiments are described in detail below.

DETAILED DESCRIPTION

Figure 1:
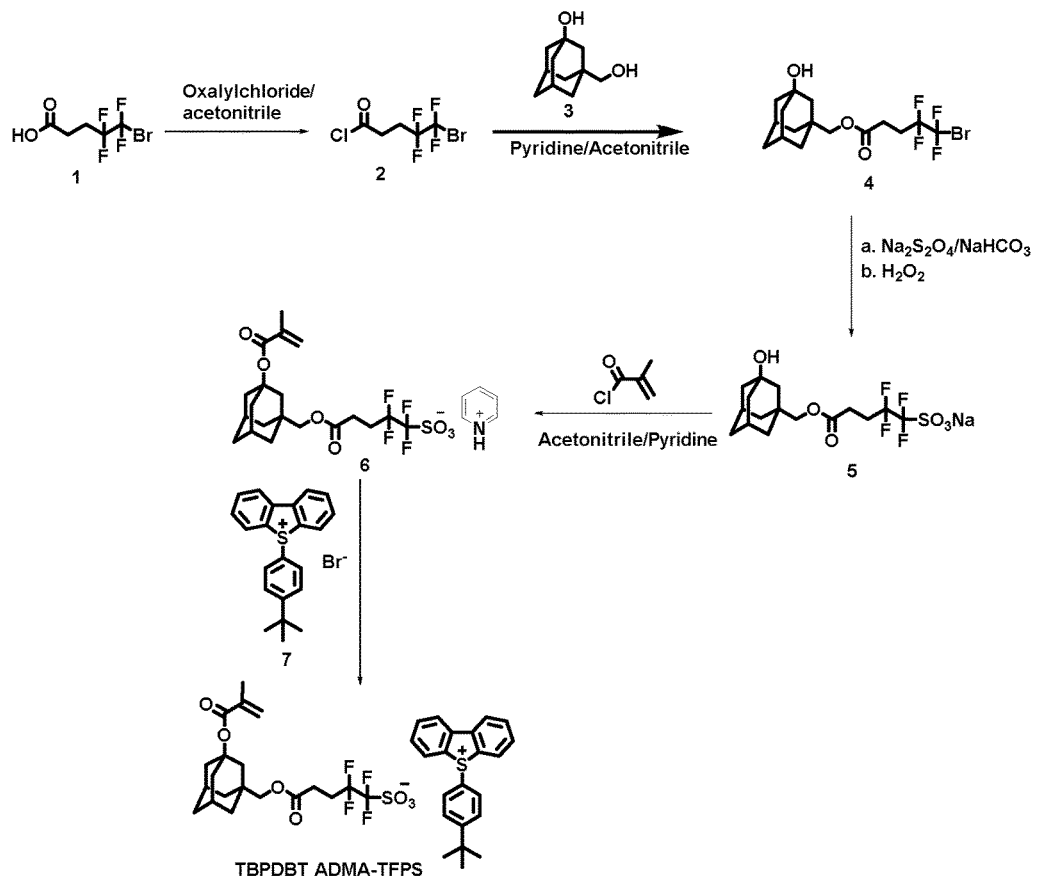
FIG. 1 is a synthetic scheme for the preparation of the monomer designated TBPDBT ADMA-TFPS.

The present inventors have determined that a polymerizable photoacid generator having a particular structure can be polymerized or copolymerized with one or more other monomers to yield a polymer-bound PAG. A photoresist composition incorporating the polymer-bound PAG exhibits resolution of features on the scale of 20 to 26 nanometers or smaller, while providing low unexposed film thickness loss, and acceptable photospeed, pattern collapse margin, exposure latitude, and line width roughness.

One embodiment is a monomer having the structure

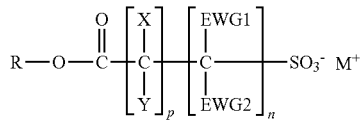

wherein R is an organic group comprising a polymerizable carbon-carbon double bond or carbon-carbon triple bond; X and Y are independently at each occurrence hydrogen or a non-hydrogen substituent; EWG1 and EWG2 are independently at each occurrence an electron-withdrawing group; p is 0, 1, 2, 3, or 4, provided that p is 1, 2, 3, or 4 when EWG1 and EWG2 are each independently fluoro, trifluoromethyl, or pentafluoroethyl; n is 1, 2, 3, or 4; and M$^+$ is an organic cation. This monomer is sometimes referred to herein as the PAG monomer.

As stated above, R is an organic group comprising (i.e., including within its structure) a polymerizable carbon-carbon double bond or carbon-carbon triple bond. In some embodiments, the R may be an organic group represented by formula (A)-(B)-, wherein (A) is a moiety selected from the group consisting of $C_{2-12}$ alkenyl, $C_{2-12}$ alkynyl, acryloyl, 2-($C_{1-12}$-alkyl)acryloyl, 2-($C_{1-12}$-fluoroalkyl)acryloyl, 2-cyanoacryloyl, and 2-fluoroacryloyl, and (B) is an optional moiety selected from the group consisting of a straight chain or branched $C_{1-20}$ alkylene group, a monocyclic or polycyclic $C_{3-20}$ cycloalkylene group, a monocyclic or polycyclic $C_{3-20}$ heterocycloalkylene group, a monocyclic or polycyclic $C_{6-20}$ arylene group, a monocyclic or polycyclic $C_{1-20}$ heteroarylene group, and any combination thereof, wherein the monocyclic or polycyclic $C_{3-20}$ heterocycloalkylene group, the monocyclic or polycyclic $C_{6-20}$ arylene group may be optionally substituted. As used herein, the term "fluoroalkyl" refers to an alkyl group comprising at least one fluoro substituent. The fluoroalkyl can be partially fluorinated or perfluorinated.

As used herein, "substituted" means including at least one substituent such as a halogen (i.e., F, Cl, Br, I), hydroxyl, amino, thiol, carboxyl, carboxylate, amide, nitrile, sulfide, disulfide, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl. It will be understood that any group or structure disclosed with respect to the formulas herein may be so substituted unless otherwise specified. Also, "fluorinated" means having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as —$CF_3$, —$C_2F_5$, —$C_3F_7$, or —$C_4F_9$). It will be understood that carbon counts for substituted groups include any carbon atoms of substituents. For example, the $C_{1-8}$-alkylene group in "substituted —C(=O)—($C_{1-8}$-alkylene)-C(=O)—" has 1 to 8 carbon atoms, including any carbon atoms derived from substitution.

In some embodiments, R is selected from the group consisting of

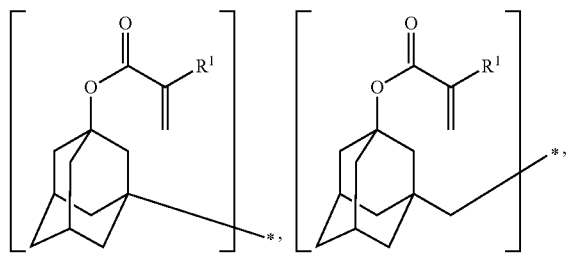

-continued

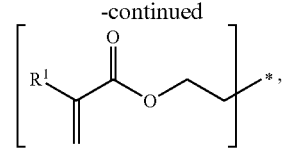

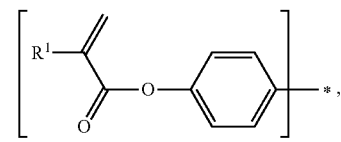

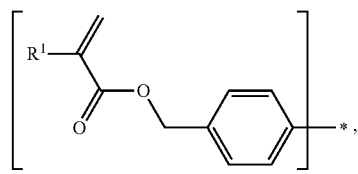

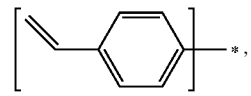

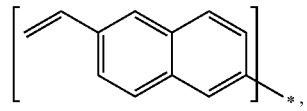

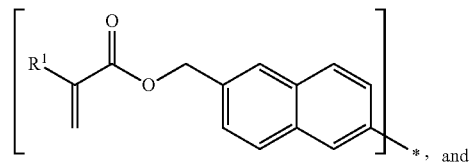

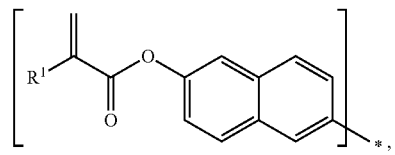

wherein $R^1$ is hydrogen, fluoro, cyano, $C_{1-10}$ alkyl, or $C_{1-10}$ fluoroalkyl.

As stated above, X and Y are independently at each occurrence hydrogen or a non-hydrogen substituent. Non-hydrogen substituents include, for example, optionally substituted alkyl including optionally substituted $C_{1-30}$alkyl; optionally substituted cycloalkyl including $C_{3-30}$ cycloalkyl; optionally substituted alkoxyl including optionally substituted $C_{1-30}$alkoxyl; optionally substituted carbo cyclic including $C_{6-30}$ carbocyclic group; optionally substituted heteroalicyclic including $C_{3-30}$ heteroalicyclic that contains 1, 2, or 3 nitrogen, oxygen, or sulfur ring atoms. In some embodiments, p is 1, 2, 3, or 4; and X and Y are hydrogen.

In the monomer structure, p is 0, 1, 2, 3, or 4, provided that p is 1, 2, 3, or 4 when EWG1 and EWG2 are each independently fluoro, trifluoromethyl, or pentafluoroethyl; and n is 1, 2, 3, or 4. In some embodiments, p is 1, 2, 3, or 4, or 1, 2, or 3. In some embodiments, n is 1, 2, or 3, or n is 1 or 2. In some embodiments, the sum of n and p is at least 2, or at least 3, or at least 4.

As stated above, EWG1 and EWG2 are independently at each occurrence an electron-withdrawing group (EWG). An electron-withdrawing group is a group that draws electron density from neighboring atoms towards itself by a resonance effect, an inductive effect, a hyperconjugation effect, or a combination thereof. The EWG may be a weakly electron-withdrawing group, a moderately electron-withdrawing group or a strongly electron-withdrawing group. The EWG can be, for example, a halogen atom (e.g., fluorine), partially halogenated or perhalogenated alkyl (e.g., —CF$_3$, —CF$_2$CF$_3$, —CCl$_3$), typically C$_{1-10}$, C$_{1-5}$ or C$_{1-3}$ partially fluorinated or perfluorinated alkyl, an aldehyde (—CHO), ketone (—COR$^{11}$), carboxylic acid (—CO$_2$H), ester (—CO$_2$R$^{11}$), amide (e.g., —CONH$_2$), cyano (—CN), sulfone (—SO$_2$R$^{11}$), sulfonate (—SO$_3$H), or nitro (—NO$_2$), wherein R$^{11}$ is independently at each occurrence a C$_{1-30}$ aliphatic organic group, a C$_{6-30}$ aromatic organic group, or a C$_{1-30}$ heteroaromatic organic group. For example, in some embodiments, EWG1 and EWG2 are independently at each occurrence an electron-withdrawing group selected from F, CF$_3$, —CN, —NO$_2$, —C(=O)R$^{11}$, —C(=O)OR$^{11}$, and —SO$_2$R$^{11}$, wherein R$^{11}$ is defined as above. In some embodiments, EWG1 or EWG2 or both EWG1 and EWG2 are fluorine or perfluoroalkyl. In some embodiments, EWG1 or EWG2 or both EWG1 and EWG2 are cyano.

In the monomer structure, M$^+$ is an organic cation. Organic cations include, for example, ammonium ion substituted with 1 to 4 alkyl groups, aryl groups, or a combination of alkyl and aryl groups; iodonium ions substituted with 2 alkyl groups, aryl groups or a combination of alkyl and aryl groups; and sulfonium ion substituted with 3 alkyl groups, aryl groups, or a combination of alkyl or aryl groups. In some embodiments, M$^+$ is an iodonium ion substituted with 2 alkyl groups, aryl groups or a combination of alkyl and aryl groups; or a sulfonium ion substituted with 3 alkyl groups, aryl groups, or a combination of alkyl or aryl groups.

Specific examples of substituted iodonium ions include diphenyliodonium,

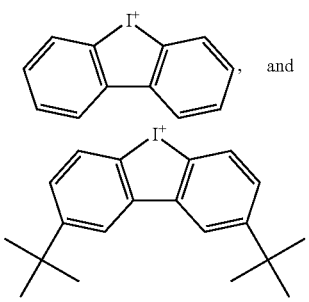

and

In some embodiments, M+ is a substituted sulfonium ion having the structure

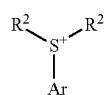

wherein, each R$^2$ is independently a C$_{1-20}$ alkyl group, a C$_{1-20}$ fluoroalkyl group, a C$_{3-20}$ cycloalkyl group, a C$_{3-20}$ fluorocycloalkyl group, a C$_{2-20}$ alkenyl group, a C$_{2-20}$ fluoroalkenyl group, a C$_{6-20}$ aryl group, a C$_{6-20}$ fluoroaryl group, a C$_{1-20}$ heteroaryl group, a C$_{7-20}$ aralkyl group, a C$_{7-20}$ fluoroaralkyl group, a C$_{2-20}$ heteroaralkyl group, or a C$_{2-20}$ fluoroheteroaralkyl group, each of which is substituted or unsubstituted, wherein each R$^2$ is either separate or connected to the other group R$^2$ via a single bond or a linking group to form a ring; and Ar is a substituted or unsubstituted C$_{6-30}$ aromatic organic group.

In some embodiments, M$^+$ has the structure

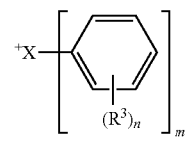

wherein X is I or S; each R$^3$ is independently a halogen, —CN, —OH, a C$_{1-10}$ alkyl group, a C$_{1-10}$ fluoroalkyl group, a C$_{1-10}$ alkoxy group, a C$_{1-10}$ fluoroalkoxy group, a C$_{3-10}$ cycloalkyl group, a C$_{3-10}$ fluorocycloalkyl group, a C$_{3-10}$ cycloalkoxy group, or a C$_{3-10}$ fluorocycloalkoxy group; each n is an integer of 0, 1, 2, 3, 4, and 5, provided that when X is I, at least one n is not 0; and m is an integer of 2 or 3, provided that when X is I, m is 2, and when X is S, m is 3.

In some embodiments, M$^+$ has the structure wherein R$^4$, R$^5$, R$^6$, R$^7$, R$^8$, R$^9$, and R$^{10}$ are each independently a halogen, —CN, —OH, a C$_{1-10}$ alkyl group, a C$_{1-10}$ fluoroalkyl group, a C$_{1-10}$ alkoxy group, a C$_{1-10}$ fluoroalkoxy group, a C$_{3-10}$ cycloalkyl group, a C$_{3-10}$ fluorocycloalkyl group, a C$_{3-10}$ cycloalkoxy group, or a C$_{3-10}$ fluorocycloalkoxy group, each of which except a halogen, —CN, and —OH may be substituted or unsubstituted; J is a single bond or a connecting group selected from S, O, and C=O; each occurrence of p is independently an integer of 0, 1, 2, 3, or 4; r is 0, 1, 2, 3, 4, or 5; and s and t are each independently 0, 1, 2, 3, or 4. R$^3$, R$^6$, R$^7$, R$^8$, R$^9$, and R$^{10}$ may optionally comprise an acid cleavable group, for example, a C$_{6-10}$ alkoxycarbonylalkyleneoxy group. An example of a C$_{6-10}$ alkoxycarbonylalkyleneoxy group is t-butyloxycarbonylmethoxy group as shown in the following compounds:

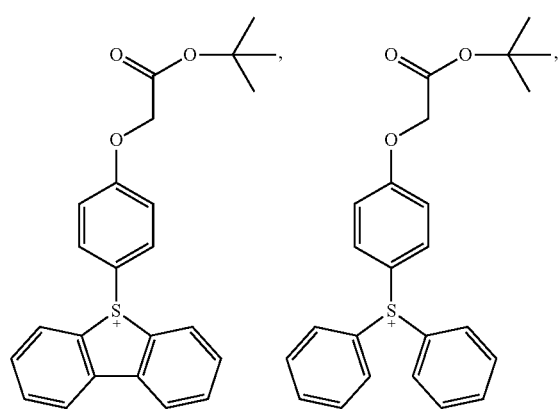
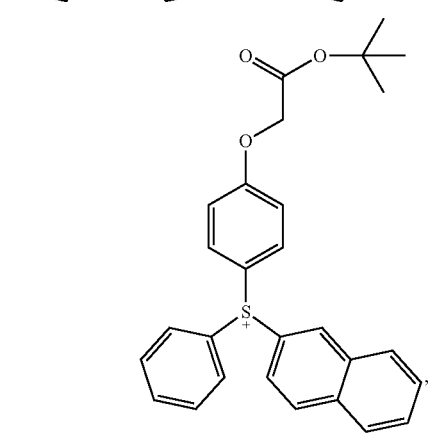
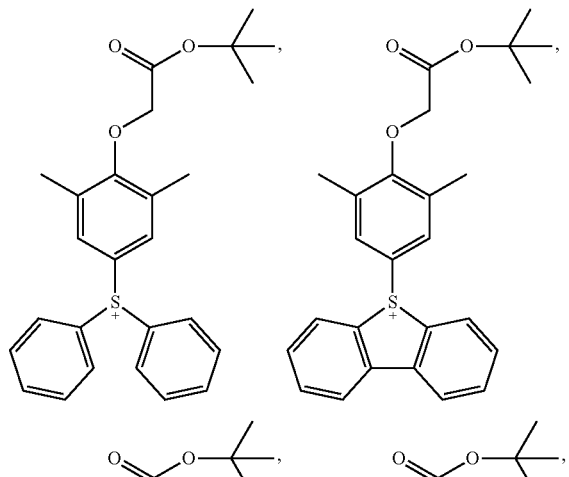
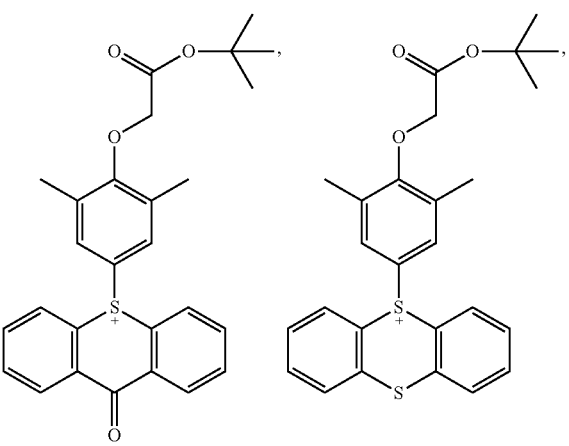
In some embodiments, M⁺ is a sulfonium ion having one of the following structures:
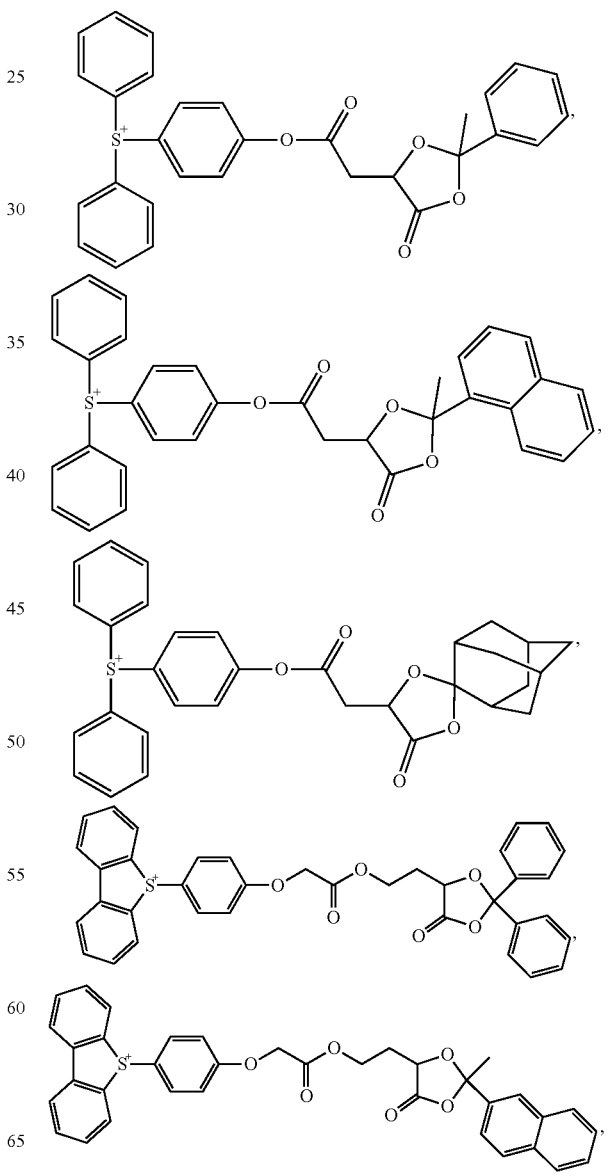

-continued

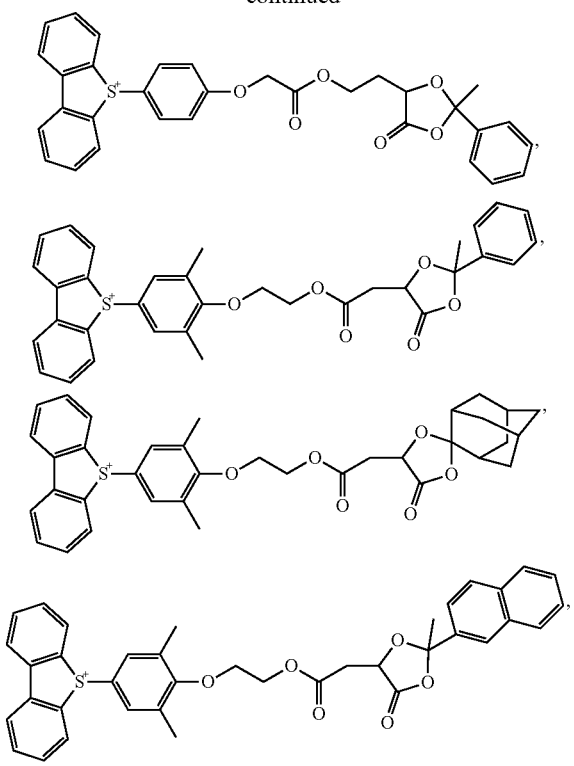

In some embodiments, M⁺ is triphenylsulfonium, S-phenyldibenzothiophenium, S-(4-t-butylphenyl)dibenzothiophenium, or

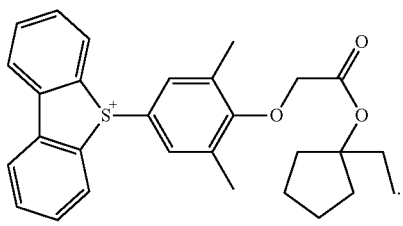

Sulfonium cations based on S-phenyldibenzothiophenium have the advantage of possessing low outgassing properties when exposed to actinic radiation, and in particular, when exposed to radiation for advanced lithographies, such as for e-beam, x-ray, and extreme ultraviolet (EUV) radiation. They are also less sensitive to out-of-band (OOB) radiation. See, e.g., U.S. Patent Application Publication No. US 2012/0171616 A1 of Thackeray et al. Sulfonium cations substituted with acid cleavable groups have the advantages of reducing unexposed film loss and improving contrast in the exposed region.

In some embodiments, the monomer has the structure

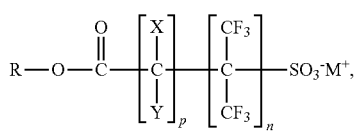

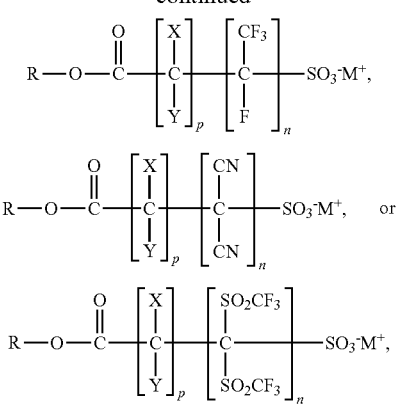

wherein R is an organic group comprising a polymerizable carbon-carbon double bond or carbon-carbon triple bond; X and Y are independently at each occurrence hydrogen or a non-hydrogen substituent; p is 0, 1, 2, 3, or 4, provided that p is 1, 2, 3, or 4 in the first and second structures above; n is 1, 2, 3, or 4; and M⁺ is an organic cation.

In some embodiments, the monomer has the structure

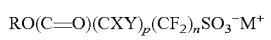

wherein R is an organic group comprising a polymerizable carbon-carbon double bond or carbon-carbon triple bond; X and Y are independently at each occurrence hydrogen or a non-hydrogen substituent; p is 0, 1, 2, 3, or 4, and n is 1, 2, 3, or 4, provided that the sum of n and p is at least 2, or at least 3; and M⁺ is an organic cation.

In some embodiments, the monomer has the structure

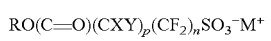

wherein R is an organic group comprising a polymerizable carbon-carbon double bond or carbon-carbon triple bond; X and Y are hydrogen; p is 1, 2, 3, or 4; n is 1, 2, 3, or 4; and M⁺ is an organic cation.

In some embodiments, the monomer is selected from the group consisting of

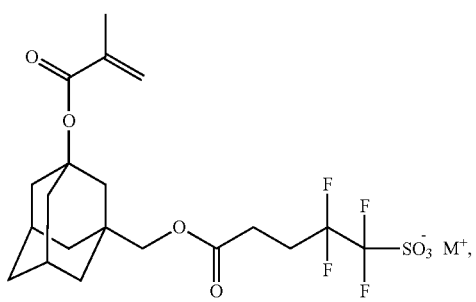

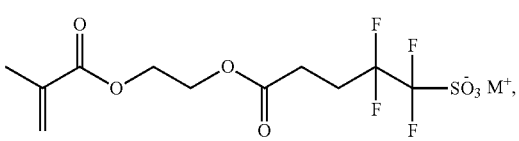

-continued

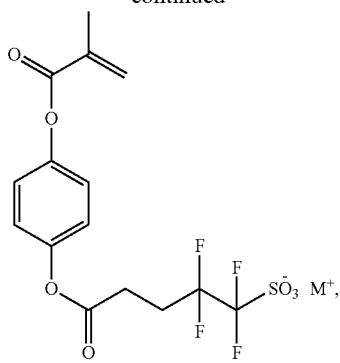

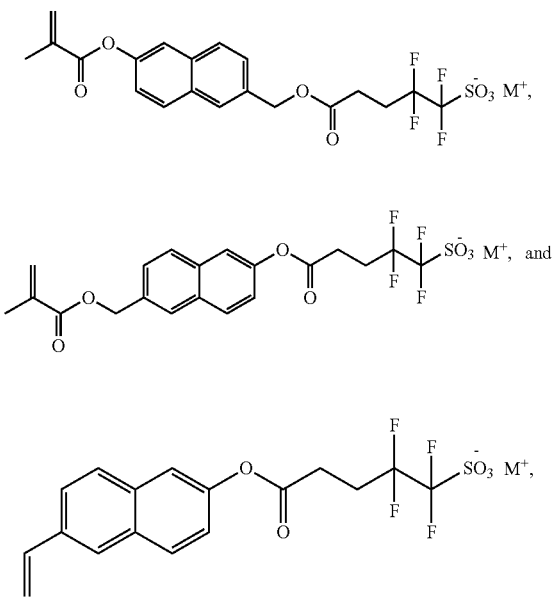

wherein M⁺ is an organic cation.

In some embodiments, the monomer is selected from the group consisting of

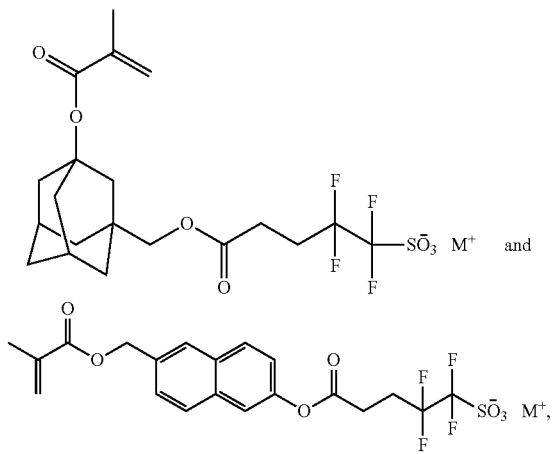

wherein M⁺ is an organic cation.

In some embodiments, the monomer has the structure

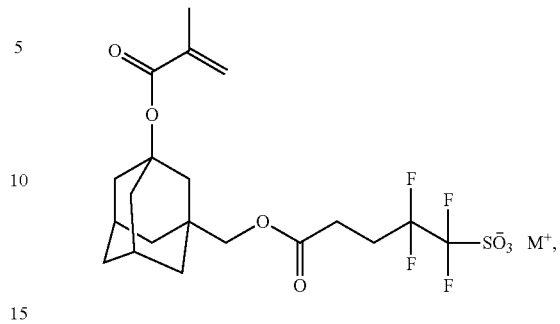

wherein $M^+$ is an organic cation. Monomers in which R includes a relatively large, non-polar group such as adamantane have the advantage of exhibiting lower unexposed film thickness loss (UFTL) than monomers without such groups.

In some embodiments, the monomer has the structure

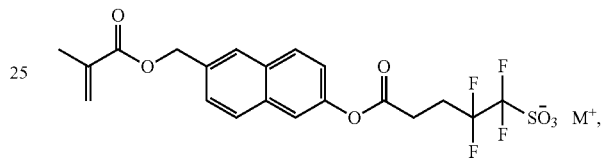

wherein $M^+$ is an organic cation. Monomers in which R includes an aromatic group such as naphthalene absorb light in the deep ultraviolet region (e.g., 193 nm, 248 nm). This is an advantage in EUV lithography, where out-of-band (OOB) deep ultraviolet radiation can deteriorate lithographic performance One embodiment is a polymer comprising repeat units derived from the PAG monomer in any of its above-described variations. This polymer is sometimes referred to herein as the Polymer-bound PAG (PBP). The PBP can be a homopolymer of one species of the PAG monomer, a copolymer of two or more species of the PAG monomer, or a copolymer of one or more species of the PAG monomer and one or more species of other monomer types. Other monomer types include, for example, acid-labile monomers, base-labile monomers, and base-ionizable monomers.

Acid-labile monomers can include, for example, a tertiary ester group, an acetal group, a ketal group, or a combination thereof. Acid-labile monomers with tertiary ester groups include

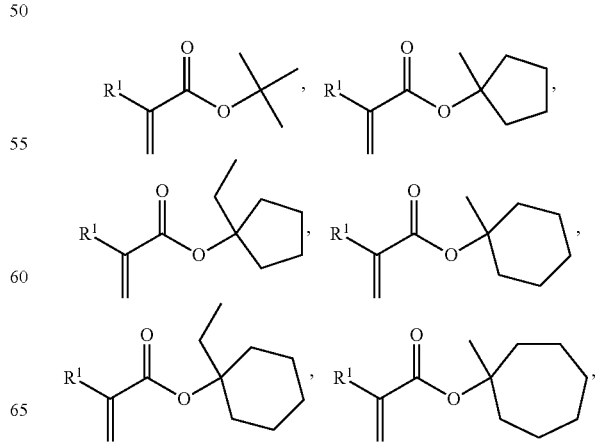

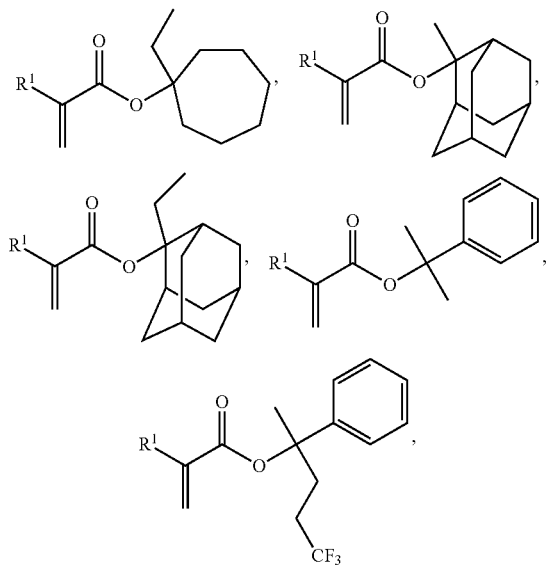
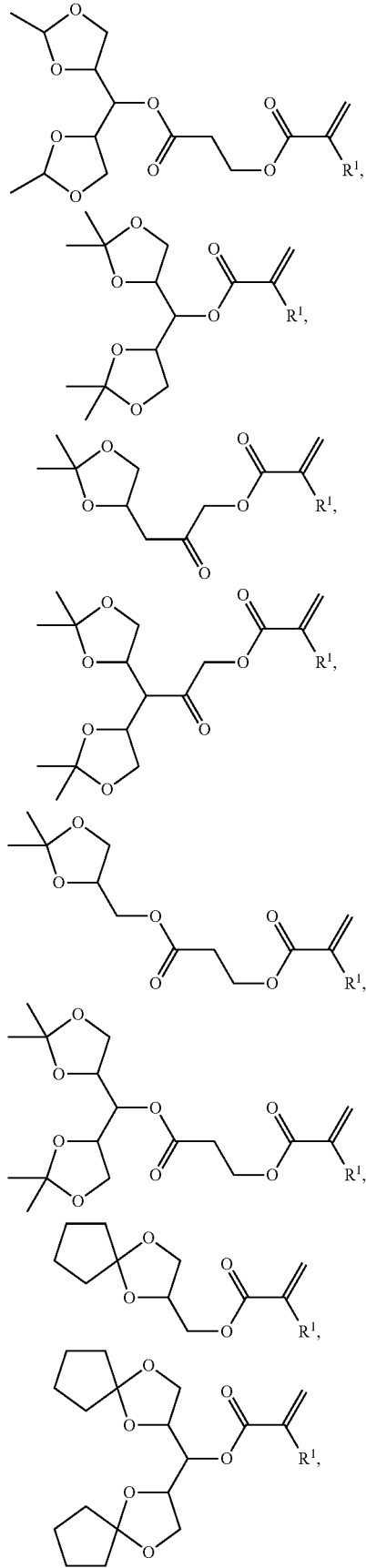
and combinations thereof, wherein $R^1$ is hydrogen, fluoro, cyano, $C_{1-10}$ alkyl, or $C_{1-10}$ fluoroalkyl.
Acid-labile monomers with acetal or ketal groups include
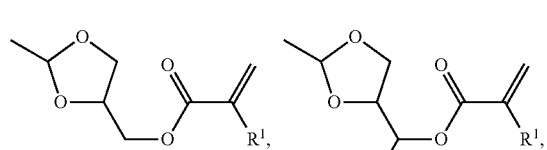
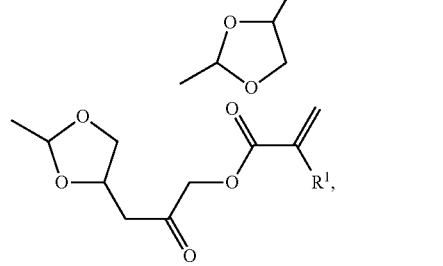
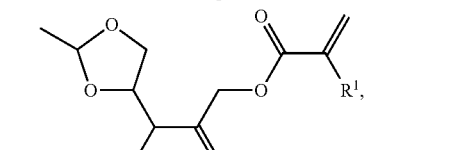
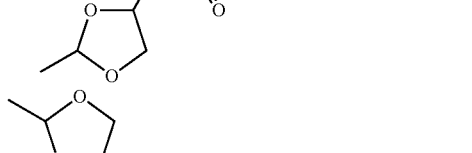
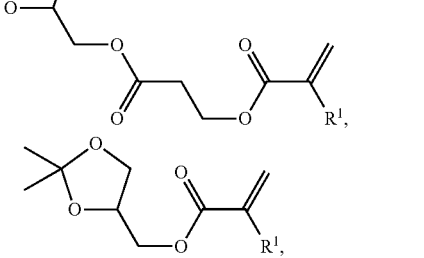

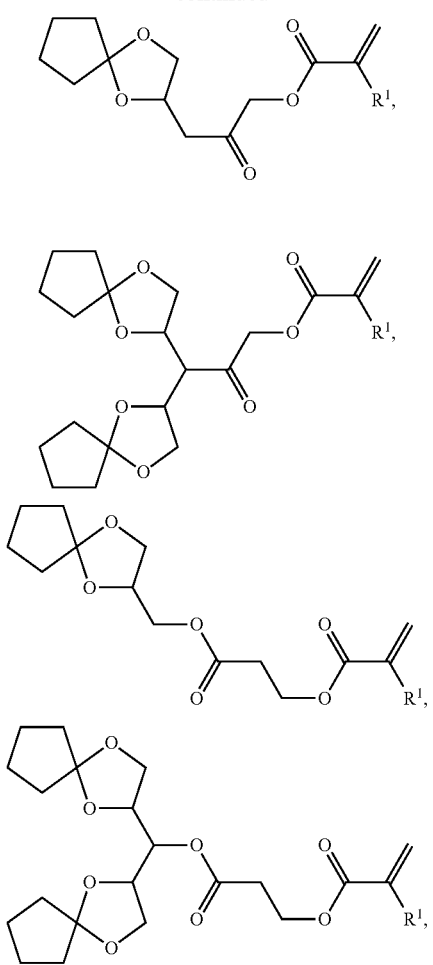

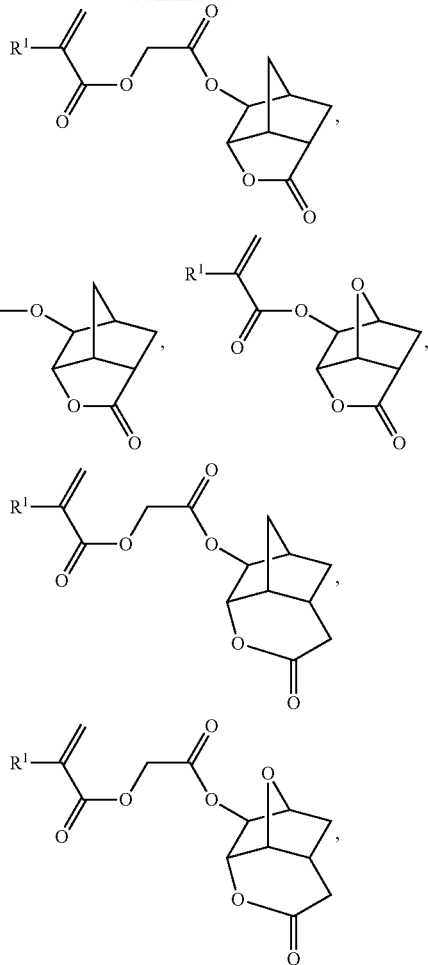

and combinations thereof, wherein $R^1$ is hydrogen, fluoro, cyano, $C_{1-10}$ alkyl, or $C_{1-10}$ fluoroalkyl.

Base-labile monomers include lactone-containing monomers. Examples of lactone-containing monomers include

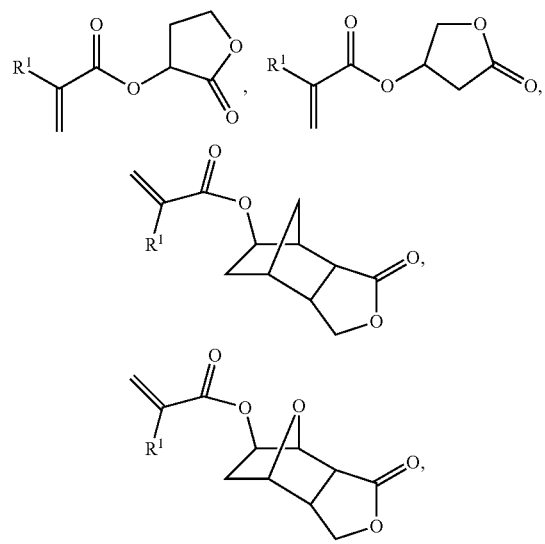

and combinations thereof, wherein $R^1$ is hydrogen, fluoro, cyano, $C_{1-10}$ alkyl, or $C_{1-10}$ fluoroalkyl.

Base-ionizable monomers have a $pK_a$ less than or equal to 12, measured at 25° C. and 1 weight percent in dimethylsulfoxide. Within this limit, the $pK_a$ can be 6 to 12, or 7 to 11, or 7 to 10. In some embodiments, the base-ionizable monomer comprises a phenol group, a sulfonamide group, or a 1,1,1,3,3,3-hexafluoro-2-hydroxy-prop-2-yl group. Specific examples of base-ionizable monomers include

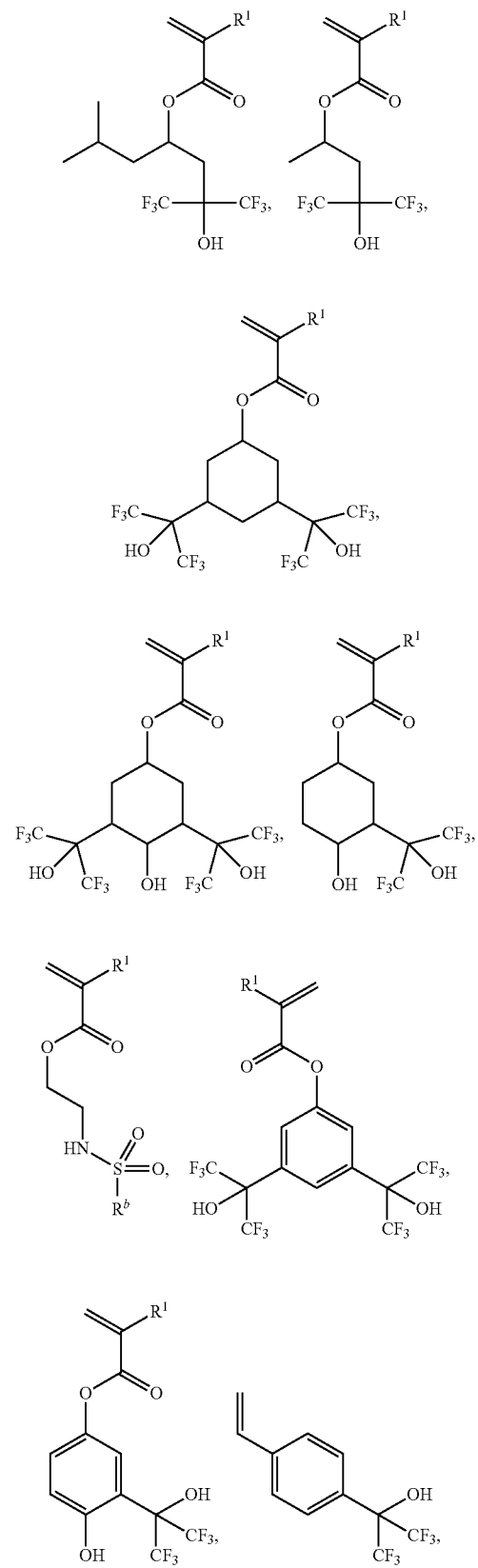

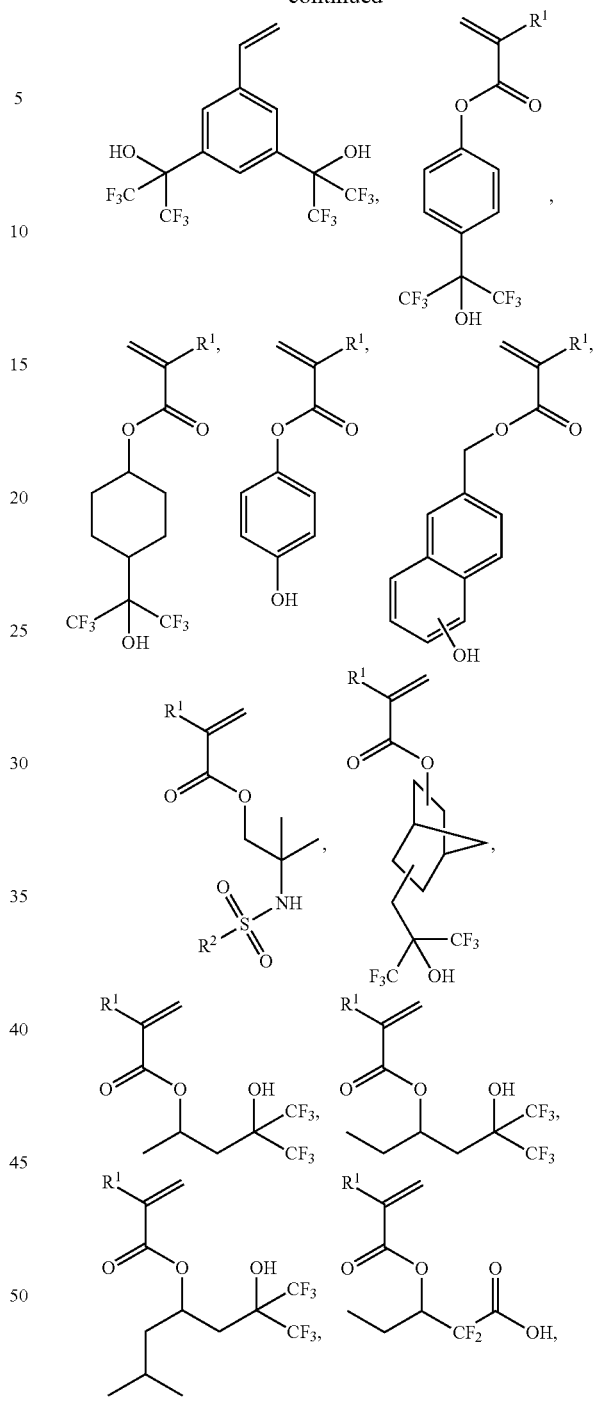

-continued and combinations thereof, wherein $R^1$ is hydrogen, fluoro, cyano, $C_{1-10}$ alkyl, or $C_{1-10}$ fluoroalkyl, and $R^2$ is $C_{1-4}$ perfluoroalkyl.

In some embodiments, the PBP comprises repeat units derived from the PAG monomer and further comprises repeat units derived from at least one of, or at least two of, or all three of, acid-labile monomers, base-labile monomers, and base-ionizable monomers. In a very specific embodiment, the PBP is a copolymer comprising 2 to 20 mole percent, or 3 to 15 mole percent, of repeat units derived from the PAG monomer; 20 to 60 mole percent, or 30 to 55 mole percent, of repeat units derived from an acid-labile monomer; 25 to 65 mole percent, or 30 to 60 mole percent, of repeat units derived from a base-labile monomer; and 2 to 20 mole percent, or 4 to 15 mole percent, of repeat units derived from a base-ionizable monomer.

One embodiment is a photoresist composition comprising the PBP, in all of its above-described variations. In some embodiments, the PBP is the only polymer in the photoresist composition. In other embodiments, the photoresist composition further comprises additional polymers.

The photoresist composition can further include one or more photoactive components such as non-polymeric photoacid generators, photobase generators, photoinitiators, additional polymers with or without bound photoacid generators, and combinations thereof.

Non-polymeric photoacid generators generally include those photoacid generators suitable for the purpose of preparing photoresists. Photoacid generators include, for example, non-ionic oximes and various onium ion salts. Onium ions include, for example, unsubstituted and substituted ammonium ions, unsubstituted and substituted phosphonium ions, unsubstituted and substituted arsonium ions, unsubstituted and substituted stibonium ions, unsubstituted and substituted bismuthonium ions, unsubstituted and substituted oxonium ions, unsubstituted and substituted sulfonium ions, unsubstituted and substituted selenonium ions, unsubstituted and substituted telluronium ions, unsubstituted and substituted fluoronium ions, unsubstituted and substituted chloronium ions, unsubstituted and substituted bromonium ions, unsubstituted and substituted iodonium ions, unsubstituted and substituted aminodiazonium ions (substituted hydrogen azide), unsubstituted and substituted hydrocyanonium ions (substituted hydrogen cyanide), unsubstituted and substituted diazenium ions ($RN=N^+R_2$), unsubstituted and substituted iminium ions ($R_2C=N^+R_2$), quaternary ammonium ions having two double-bonded substituents ($R=N^+=R$), nitronium ion ($NO_2^+$), bis(triarylphosphine)iminium ions ($(Ar_3P)_2N^+$), unsubstituted or substituted tertiary ammonium having one triple-bonded substituent ($R\equiv NH^+$), unsubstituted and substituted nitrilium ions ($RC\equiv NR^+$), unsubstituted and substituted diazonium ions ($N\equiv N^+ R$), tertiary ammonium ions having two partially double-bonded substituents ($R\!=\!=\!=\!N^+H\!=\!=\!=\!R$), unsubstituted and substituted pyridinium ions, quaternary ammonium ions having one triple-bonded substituent and one single-bonded substituent ($R\equiv N^+R$), tertiary oxonium ions having one triple-bonded substituent ($R\equiv O^+$), nitrosonium ion ($N\equiv O^+$), tertiary oxonium ions having two partially double-bonded substituents ($R\!=\!=\!=\!O^+\!=\!=\!=\!R$), pyrylium ion ($C_5H_5O^+$), tertiary sulfonium ions having one triple-bonded substituent ($R\equiv S^+$), tertiary sulfonium ions having two partially double-bonded substituents ($R\!=\!=\!=\!S^+\!=\!=\!=\!R$), and thionitrosonium ion ($N\equiv S^+$). In some embodiments, the onium ion is selected from unsubstituted and substituted diaryiodonium ions, and unsubstituted and substituted triarylsulfonium ions. Examples of suitable onium salts can be found in U.S. Pat. No. 4,442,197 to Crivello et al., U.S. Pat. No. 4,603,101 to Crivello, and U.S. Pat. No. 4,624,912 to Zweifel et al.

Suitable non-polymeric photoacid generators include, for example, onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl-p-toluenesulfonate, 2,6-dinitrobenzyl-p-toluenesulfonate, and 2,4-dinitrobenzyl-p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenesulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. Suitable non-polymeric photoacid generators are further described in U.S. Pat. No. 8,431,325 to Hashimoto et al. in column 37, lines 11-47 and columns 41-91.

The photoresist composition can include a photoinitiator. Photoinitiators are used in the photoresist composition for initiating polymerization of the cross-linking agents by generation of free-radicals. Suitable free radical photoinitiators include, for example, azo compounds, sulfur containing compounds, metallic salts and complexes, oximes, amines, polynuclear compounds, organic carbonyl compounds and mixtures thereof as described in U.S. Pat. No. 4,343,885, column 13, line 26 to column 17, line 18; and 9,10-anthraquinone; 1-chloroanthraquinone; 2-chloroanthraquinone; 2-methylanthraquinone; 2-ethylanthraquinone; 2-tert-butylanthraquinone; octamethylanthraquinone; 1,4-naphthoquinone; 9,10-phenanthrenequinone; 1,2-benzanthraquinone; 2,3-benzanthraquinone; 2-methyl-1,4-naphthoquinone; 2,3-dichloronaphthoquinone; 1,4-dimethylanthraquinone; 2,3-dimethylanthraquinone; 2-phenylanthraquinone; 2,3-diphenylanthraquinone; 3-chloro-2-methylanthraquinone; retenequinone; 7,8,9,10-tetrahydronaphthalenequinone; and 1,2,3,4-tetrahydrobenz(a)anthracene-7,12-dione. Other photoinitiators are described in U.S. Pat. No. 2,760,863 and include vicinal ketaldonyl alcohols, such as benzoin, pivaloin, acyloin ethers, e.g., benzoin methyl and ethyl ethers; and alpha-hydrocarbon-substituted aromatic acyloins, including alpha-methylbenzoin, alpha-allylbenzoin, and alpha-phenylbenzoin. Photoreducible dyes and reducing agents disclosed in U.S. Pat. Nos. 2,850,445; 2,875,047; and 3,097,096 as well as dyes of the phenazine, oxazine, and quinone classes; benzophenone, 2,4,5-triphenylimidazolyl dimers with hydrogen donors, and mixtures thereof as described in U.S. Pat. Nos. 3,427,161; 3,479,185; and 3,549,367 can be also used as photoinitiators.

The photoresist composition can further include a surfactant. Illustrative surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLY-FOX™ PF-636, PF-6320, PF-656, and PF-6520 fluorosurfactants from Omnova.

The photoresist composition can further include quenchers that are non-photo-destroyable bases. These include, for example, those based on hydroxides, carboxylates, amines, imines and amides. Such quenchers include $C_{1-30}$ organic amines, imines or amides, $C_{1-30}$ quaternary ammonium salts of strong bases (e.g., a hydroxide or alkoxide) or a weak base (e.g., a carboxylate). In some embodiments, the photoresist composition further comprises a quencher selected from the group consisting of $C_{1-30}$ amines, $C_{1-30}$ amides, and combinations thereof. Exemplary quenchers include amines such as Troger's base; hindered amines such as diazabicycloundecene (DBU), diazabicyclononene (DBN), and tetrahydroxy isopropyl diamine and tert-butyl-4-hydroxy-1-piperidiene carboxylate; ionic quenchers including quaternary alkyl ammonium salts such as tetrabutylammonium hydroxide (TBAH), tetramethylammonium 2-hydroxybenzoic acid (TMA OHBA), and tetrabutylammonium lactate. Suitable quenchers are further described in U.S. Pat. No. 8,431,325 to Hashimoto et al.

The photoresist composition components are typically dissolved in a solvent for dispensing and coating. Exemplary solvents include anisole; alcohols including 1-methoxy-2-propanol, and 1-ethoxy-2-propanol; esters including n-butyl acetate, ethyl lactate, 1-methoxy-2-propyl acetate, methoxyethoxy propionate, and ethoxyethoxy propionate; ketones including cyclohexanone and 2-heptanone; and combinations thereof. The solvent amount can be, for example, 70 to 99 weight percent, specifically 85 to 98 weight percent, based on the total weight of the photoresist composition.

The invention further includes a method of forming a photoresist relief image, comprising: (a) applying a layer of the photoresist composition on a substrate to form a photoresist layer; (b) pattern-wise exposing the photoresist layer to activating radiation to form an exposed photoresist layer; and (c) developing the exposed photoresist layer to provide a photoresist relief image. The method can, optionally, further include (d) etching the resist relief pattern into the underlying substrate.

The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, having one or more layers and patterned features formed on a surface thereof. Optionally, the underlying base substrate material itself may be patterned, for example, when it is desired to form trenches in the base substrate material. Layers formed over the base substrate material may include, for example, one or more conductive layers such as layers of aluminum, copper, molybdenum, tantalum, titanium, tungsten, and alloys, nitrides or silicides of such metals, doped amorphous silicon or doped polysilicon, one or more dielectric layers such as layers of silicon oxide, silicon nitride, silicon oxynitride or metal oxides, semiconductor layers, such as single-crystal silicon, underlayers, antireflective layers such as a bottom antireflective layers, and combinations thereof. The layers can be formed by various techniques, for example, chemical vapor deposition (CVD) such as plasma-enhanced CVD, low-pressure CVD or epitaxial growth, physical vapor deposition (PVD) such as sputtering or evaporation, electroplating or spin-coating.

Applying the photoresist composition to the substrate can be accomplished by any suitable method, including spin coating, spray coating, dip coating, and doctor blading. In some embodiments, applying the layer of photoresist composition is accomplished by spin coating the photoresist in solvent using a coating track, in which the photoresist composition is dispensed on a spinning wafer. During dispensing, the wafer can be spun at a speed of up to 4,000 rotations per minute (rpm), specifically 500 to 3,000 rpm, and more specifically 1,000 to 2,500 rpm. The coated wafer is spun to remove solvent, and baked on a hot plate to remove residual solvent and free volume from the film to make it uniformly dense.

Pattern-wise exposure is then carried out using an exposure tool such as a stepper, in which the film is irradiated through a pattern mask and thereby is exposed pattern-wise. In some embodiments, the method uses advanced exposure tools generating activating radiation at wavelengths capable of high resolution including extreme-ultraviolet (EUV) or electron-beam (e-beam) radiation. It will be appreciated that exposure using the activating radiation decomposes the PAG in the exposed areas and generates acid and decomposition by-products, and that the acid then effects a chemical change in the polymer (deblocking the acid sensitive groups to generate a base-soluble group) during the post exposure bake (PEB) step. The resolution of such exposure tools can be less than 30 nanometers.

Developing the exposed photoresist layer is then accomplished by treating the exposed layer with a suitable developer capable of selectively removing the exposed portions of the film (where the photoresist is positive tone) or removing the unexposed portions of the film (where the photoresist is crosslinkable in the exposed regions, i.e., negative tone). In some embodiments, the photoresist is positive tone based on a polymer having acid-sensitive (deprotectable) groups, and the developer is preferably a metal-ion-free tetraalkylammonium hydroxide solution, such as, for example, aqueous 0.26 Normal tetramethylammonium hydroxide. Alternatively, negative tone development (NTD) can be conducted by use of a suitable organic solvent developer. NTD results in the removal of unexposed regions of the photoresist layer, leaving behind exposed regions due to polarity reversal of those regions. Suitable NTD developers include, for example, ketones, esters, ethers, hydrocarbons, and mixtures thereof. Other suitable solvents include those used in the photoresist composition. In some embodiments, the developer is 2-heptanone or a butyl acetate such as n-butyl acetate. Whether the development is positive tone or negative tone, a pattern forms by developing.

The photoresist composition can, when used in one or more such a pattern-forming processes, be used to fabricate electronic and optoelectronic devices such as memory devices, processor chips (including central processing units or CPUs), graphics chips, and other such devices.

EXAMPLES

The acronyms and chemical structures of monomers used in these examples are presented in Table 1. The synthesis of the monomer designated TBPDBT F2 is described in U.S. Patent Application Publication No. US 2012/0171616 A1 of Thackeray et al., paragraph [0072].

The synthesis of the monomer designated ECPPDBT F2 is described in U.S. Patent Application Publication No. US 2014/0080058 A1 of Cameron et al., paragraph [0072].

TABLE 1

| Monomer Acronym | Chemical Structure |
| --- | --- |
| TBPDBT F2 | 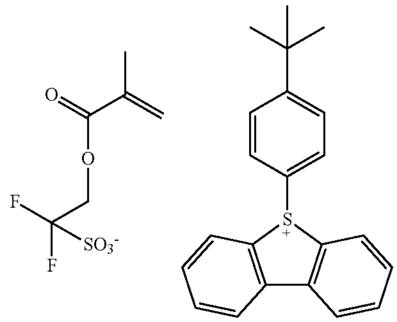 |
| ECPPDBT F2 | 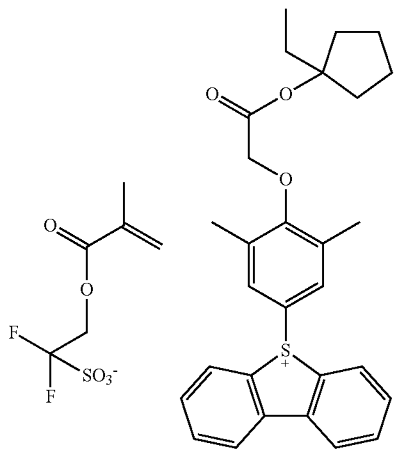 |
| TBPDBT ADMA-TFPS | 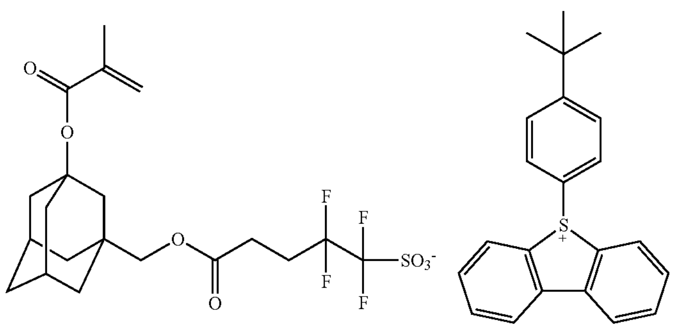 |
| ECPPDBT ADMA-TFPS | 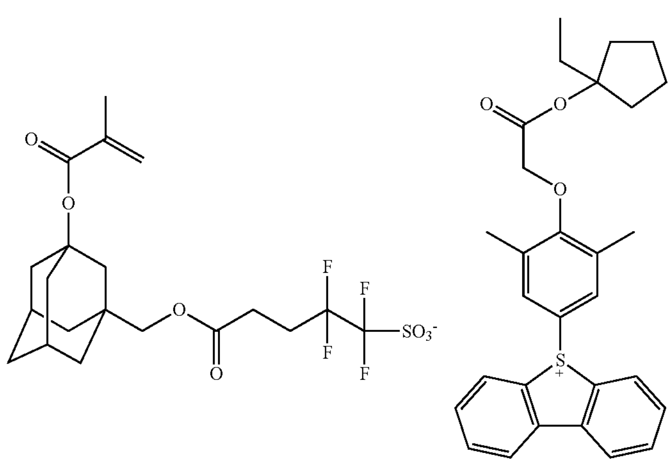 |

TABLE 1-continued

| Monomer Acronym | Chemical Structure |
| --- | --- |
| ECPPDBT HNMA-TFPS | |
| PPMA | 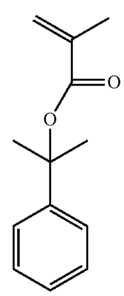 |
| FC3PPMA | 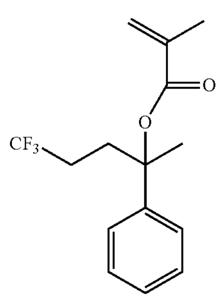 [SMILES: C=C(C)C(=O)OC(C)(CCC(F)(F)F)c1ccccc1] |
| α-GBLMA | 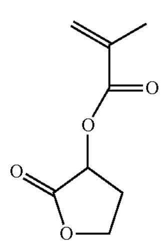 |

TABLE 1-continued

| Monomer Acronym | Chemical Structure |
|---|---|
| DiHFA | (structure: methacrylate ester of cyclohexane substituted with two -C(CF$_3$)$_2$OH groups) |

Monomer Syntheses

This example describes the synthesis of three inventive monomers. The synthetic scheme for the monomer designated TBPDBT ADMA-TFPS is summarized in FIG. 1. To a mixture of 4-bromo-4,4,5,5-tetrafluoropentanoic acid (20 g, 158.1 mmol), N,N-dimethylformamide (2.0 g, 36 mmol) in 200 mL acetonitrile was added dropwise oxalyl chloride (20 g, 157.57 mmol). The mixture was stirred at room temperature for 2 hours and then added drop-wise to a solution made of pyridine (12.4 g, 156.76 mmol) and 3-hydroxyadmantane methanol (compound 3; 28.8 g, 158.01 mmol) in 150 mL acetonitrile. The mixture was stirred at room temperature for 4 hours, then the solvent was distilled off completely under reduced pressure and the resulting residue was dissolved in 200 mL of methylene chloride and washed twice with 200 mL 0.1 N hydrochloric acid and then washed twice with 200 mL of deionized water. The organic phase was dried over MgSO$_4$, filtered, and the solvent removed completely to produce the crude product 3-hydroxyadamantan-1-yl) methyl 5-bromo-4,4,5,5-tetrafluoropentanoate (compound 4, 60 g) as colorless oil, which was used in the next step without further purification.

An aqueous solution made of sodium dithionate (41.7 g, 239.50 mol) and sodium hydrogen carbonate (30.2 g, 239.50 mol) was added to a solution of compound 4 (50 g, 119.8 mol) in 200 mL acetonitrile and the mixture was stirred at 75° C. for 16 hours. The mixture was cooled to room temperature and the lower, aqueous layer was removed. The upper, organic layer was transferred in to a flask. To the organic layer was added hydrogen peroxide (20 g of 30 weight percent solution) and the mixture was stirred at room temperature for 52 hours. The solution was filtered to remove salts and the solvents were distilled off under reduced pressure. The resulting residue was dissolved in 250 mL acetone, and the resulting solution was dried with magnesium sulfate, filtered, and the filtrate was concentrated under reduced pressure to produce a gummy-like crude product. The crude product was dissolved in 75 mL acetone and poured slowly into methyl t-butylether (750 mL), to produce 36 g of 1,1,2,2-tetrafluoro-5-((-3-hydroxyadamantan-1-yl)methoxy)-5-oxopentane-1-sulfonate sodium salt (compound 5).

To a solution of compound 5 (25.0 g, 56.766 mmol) and pyridine (7.17 g, 90.8 mmol) in 150 mL acetonitrile at 0° C. was added drop-wise a solution of methacryloyl chloride (14.85 mmol) in 100 mL acetonitrile. The mixture was stirred at 0° C. for one hour and then at room temperature for 24 hours. Liquid Chromatography-Mass Spectrometry (LC-MS) showed incomplete conversion. Pyridine (6 mL) and methacryloyl chloride (5 g) were added and the mixture was stirred for additional 4 hours at room temperature. LC-MS showed complete conversion. The salts were removed by filtration and the filtrate was concentrated under reduced pressure to produce the crude product pyridinium 1,1,2,2-tetrafluoro-5-((-3-(methacryloyloxy)adamantan-1-yl) methoxy)-5-oxopentane-1-sulfonate (compound 6) as an orange oil, which was used in the next step without further purification.

The crude compound 6 obtained from the previous step was suspended in 150 mL of water and mixed with a suspension of t-butylphenydibenzothiophenium bromide (compound 7, 14.6 g, 36.9 mmol). The resulting mixture was stirred at room temperature for 4 hours. The organic phase was separated, washed twice with 100 mL of deionized water, concentrated and poured into heptane to obtain crude product. The crude product was suspended in ethyl acetate and heated at reflux, the insoluble parts were removed by filtration, and the filtrate was cooled to room temperature to produce a precipitate, which was collected by filtration. The precipitate was suspended in 200 mL heptanes/methyl t-butylether (1:1 volume/volume (v/v)) and the mixture was stirred at room temperature for 1 hour. The target PAG monomer TBPDBT ADMA-TFPS was filtered and dried (overall yield was 12.5 g). Samples of the PAG were assayed for purity by HPLC-MS. The cation was determined to be >98.0% pure as detected by UV at 215 nm, and purity detected by positive ion mass spectrometry was >98%. The anion purity as measured by negative ion liquid chromatography mass spectrometry (LC-MS) was determined to be >98%.

Figure 2:
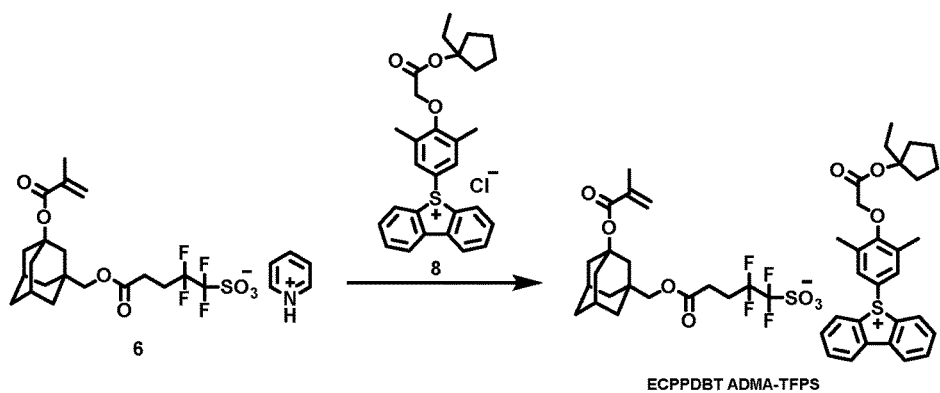
FIG. 2 is a synthetic scheme for the preparation of the monomer designated ECPPDBT ADMA-TFPS.

The synthetic scheme for the monomer designated ECPPDBT ADMA-TFPS is summarized in FIG. 2. Compound 6 (30.0 g, 53.0 mmol) was suspended in 150 mL of water and mixed with a suspension of compound 8 (18.5 g, 52.90 mmol). The resulting mixture was stirred at room temperature for 16 hours. The organic phase was separated, washed twice with 100 mL of deionized water, concentrated, and poured into heptanes to obtain crude product. The crude product was suspended in ethyl acetate and heated at reflux, the insoluble parts were removed by filtration, and the filtrate was cooled to room temperature to produce a precipitate, which was collected by filtration. The precipitate was suspended in 200 mL heptanes/methyl t-butylether (1:1 v/v), and the mixture was stirred at room temperature for 1 hour. The target PAG monomer ECPPDBT ADMA-TFPS was filtered and dried (overall yield was 17.5 g). Samples of the PAG were assayed for purity by LC-MS. The cation was determined to be >98.0% pure as detected by UV at 215 nm, and purity detected by positive ion mass spectrometry was >98%. The anion purity as measured by negative ion LC-MS was determined to be >98%.

Figure 3:
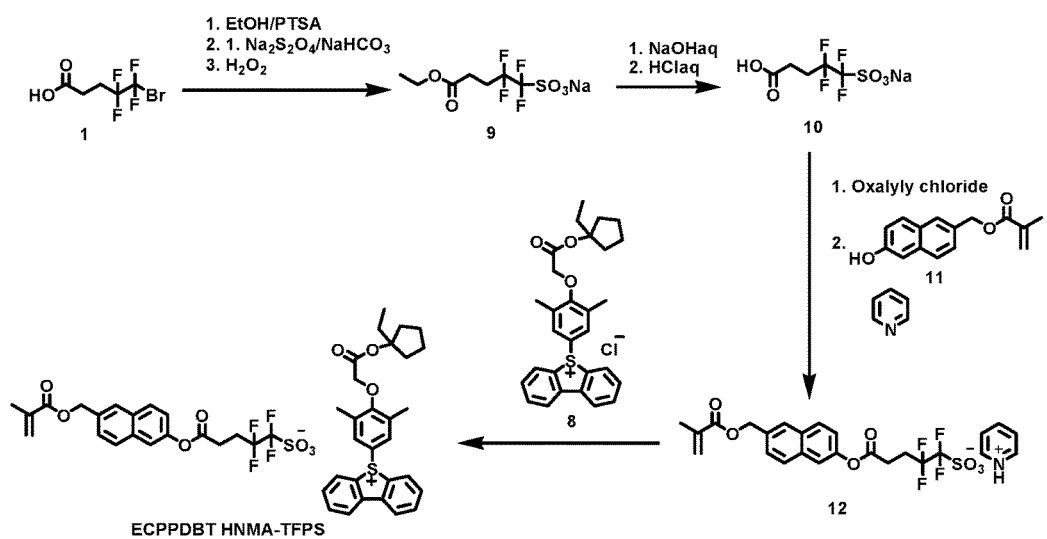
FIG. 3 is a synthetic scheme for the preparation of the monomer designated ECPPDBT HNMA-TFPS.

The synthetic scheme for the monomer designated ECPPDBT HNMA-TFPS is summarized in FIG. 3. A 500 ml round-bottomed flask was charged with 5-bromo-4,4,5,5-tetrafluoropentanoic acid (1, 35 g, 138.35 mmol) and 200 mL ethanol and 0.3 g of para-toluenesulfonic acid. The mixture was refluxed for 6 hours, then cooled to room temperature, and the solvent was fully removed under reduced pressure to produce 5-bromo-4,4,5,5-tetrafluoropentanoic acid ethylester (9) as an oily crude product. The crude product was used in the next step without further purification (assuming 100% conversion).

A solution of sodium dithionate (48.17 g, 276.69 mmol) and sodium hydrogen carbonate (34 g, 415.03 mmol) in 150 mL water was added to a solution of the crude 5-bromo-4,4,5,5-tetrafluoropentanoic acid ethylester (9) in 150 mL acetonitrile. The mixture was stirred at 70° C. for 16 hours. The organic phase was separated and the water solution was extracted with 100 mL acetonitrile. To the combined acetonitrile solutions was added 20 g of 30% hydrogen peroxide solution and the mixture was stirred at room temperature for 48 hours. Excess hydrogen peroxide was neutralized and the acetonitrile was removed under reduced pressure. The resulting residue was dissolved in 100 mL water and to the solution was added 5 g of sodium hydroxide. The mixture was refluxed for 4 hours, cooled to room temperature and acidified with concentrated hydrochloric acid until the pH was reduced to 2. The water was removed under reduced pressure until dryness to produce a solid which was suspended in acetonitrile and filtered to remove inorganics, then the acetonitrile was fully removed from the filtrate to produce 13.5 g of 4-carboxy-1,1,2,2-tetrafluorobutane-1-sulfonate sodium salt (10).

To a solution of salt (10) (8.0 g, 31.62 mmol) in 75 mL acetonitrile and 0.2 mL of dimethylformamide (DMF) was added slowly oxalylchloride (3.70 g, 29.15 mmol). The mixture was stirred at room temperature for 1 hour and then (6-hydroxynaphthalen-2-yl)methyl methacrylate (11) (7.0 g, 28.89 mmol) was added followed by 3.5 g (44.25 mmol) of pyridine. The mixture was stirred for at room temperature for 2 hours. Insoluble salts were removed by filtration, and the acetonitrile was removed under vacuum. The resulting residue was dissolved in 50 mL of acetone and added slowly to methyl tert-butyl ether (1 liter). This produced 7.3 g of compound (12) as an oily product which was used in the next step without further purification. The crude salt (12) (6.0 g, 10.76 mmol) was suspended in 75 mL of water and mixed with a suspension of compound (8) (5.3 g, 5.70 mmol) in 75 mL dichloromethane. The resulting mixture was stirred at room temperature for 16 hours. The organic phase was separated, washed twice with 50 mL of deionized water, concentrated, and poured into heptanes to obtain crude product. The crude product was purified by flash chromatography using dichloromethane/acetone with volume ratio 3:1 as an eluent. The organic solvent was removed under reduced pressure to produce 4.8 g of the target monomer ECPPDBT HNMA-TFPS. Samples of the PAG were assayed for purity by LC-MS. The cation was determined to be >98.0% pure as detected by UV at 215 nm, and purity detected by positive ion mass spectrometry was >98%. The anion purity as measured by negative ion LC-MS was determined to be >98%.

Copolymer Syntheses

This example describes the synthesis of four inventive and three comparative copolymers. Copolymer 1 was prepared from the monomers PPMA, α-GBLMA, DiHFA, and TBPDBT ADMA-TFPS at a molar feed ratio of 36.5:47.5:11:5. A feed solution was made by dissolving PPMA (12.0 g, 58.7 mmol), α-GBLMA (13.01 g, 76.5 mmol), DiHFA (8.86 g, 17.7 mmol), and TBPDBT ADMA-TFPS (6.35 g, 8.0 mmol) in 51.8 g of a 30:70 (v/v) mixture of ethyl lactate/gamma-butyrolactone. An initiator solution was prepared by dissolving 4.0 g of the azo initiator 2,2'-azobis(2,4-dimethyl valeronitrile) (obtained as V-65 from Wako Pure Chemical Industries, Ltd.) in 8 g of a 2:1 (v/v) mixture of acetonitrile/tetrahydrofuran.

The polymerization was carried out in a 2-liter, 3-neck round bottom flask fitted with a water condenser and a thermometer to monitor the reaction in the flask. The reactor was charged with 14.5 g solution of ethyl lactate/gamma-butyrolactone, and the contents were heated to 75° C. The feed solution and the initiator solution were fed into the reactor using syringe pumps over a 4 hour time period. The contents were then stirred for an additional 2 hours. The contents were cooled to room temperature, diluted with tetrahydrofuran (THF) to 25 weight percent, and precipitated into 10-fold (by weight) of a 95:5 (w/w) mixture of diisopropyl ether (IPE) and methanol (MeOH). The resulting polymer obtained was dried under vacuum at 50° C. for 24 hours to yield 32.5 g of a copolymer 1.

The polymers set forth in Table 2 were prepared using the same procedure used to make copolymer 1, except using the monomer types and molar feed ratios as specified in Table 2. The structures of the monomers listed in Table 2 are provided in Table 1.

TABLE 2

| Copolymer | Unit 1 (mole %) | Unit 2 (mole %) | Unit 3 (mole %) | Unit 4 (mole %) |
|---|---|---|---|---|
| 1 | PPMA (36.5) | α-GBLMA (47.5) | DiHFA (11.0) | TBPDBT ADMA-TFPS (5.0) |
| 2 | PPMA (36.0) | α-GBLMA (46.0) | DiHFA (10) | TBPDBT ADMA-TFPS (8.0) |
| 3 | CF3PPMA (36.5) | α-GBLMA (47.5) | DiHFA (11) | TBPDBT ADMA-TFPS (5.0) |
| 4 | PPMA (36.5) | α-GBLMA (47.5) | DiHFA (11) | ECPPDBT ADMA-TFPS (5.0) |
| 5 (comparative) | PPMA (36.5) | α-GBLMA (47.5) | DiHFA (11) | TBPDBT F2 (5.0) |
| 6 (comparative) | CF3PPMA (36.5) | α-GBLMA (47.5) | DiHFA (11) | TBPDBT F2 (5.0) |
| 7 (comparative) | PPMA (36.5) | α-GBLMA (47.5) | DiHFA (11) | ECPPDBT F2 (5.0) |

Photoresist Preparation and Processing

Photoresist compositions containing copolymers 1 and 2 were each independently formulated as summarized in Table 3. A comparative composition containing comparative copolymer 5 was prepared similarly. Component amounts in Table 3 are based on total solids, excluding solvents. The non-polymeric photoacid generator was TBPDBT DHC, which has the chemical structure

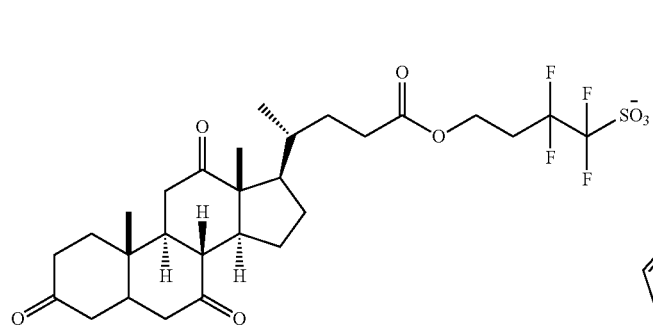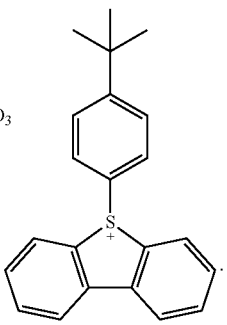

TBPDBT DHC

The quencher was triisopropylamine (TIPA). The surfactant was a fluorinated surfactant obtained as POLYFOX™ PF-656.

Compositions of two inventive and one comparative photoresist compositions are summarized in Table 3, where component amounts are expressed as weight percent based on total solids, excluding solvents.

TABLE 3

| Photoresist | Copolymer | PAG | Quencher | Surfactant |
|---|---|---|---|---|
| 1 | 62.4% Copolymer 1 | 35.5% TBPDBT DHC | 1.5% | 0.1% |
| 2 | 62.4% Copolymer 2 | 35.5% TBPDBT DHC | 1.5% | 0.1% |
| 3 (comparative) | 62.4% Copolymer 5 | 35.5% TBPDBT DHC | 1.5% | 0.1% |

All formulations in Table 3 used a 70:30 (w/w) mixture of ethyl lactate/methyl 2-hydroxyisobutyrate as solvent. The resists were processed at a soft bake of 110° C. for 90 seconds and a post-exposure base at 100° C. for 60 seconds. Contrast curves at 248 nanometers were generated by coating the resist on a 60 nanometer thick organic antireflective layer (Dow Electronic Materials AR™ 9-900). The resist was exposed at 248 nanometers on a Canon TELACT tool. After post-exposure bake, the resists were developed for 60 seconds using 0.26 Normal tetramethylammonium hydroxide solution. Film thickness values were measured using KLA Tencore OPTIPROBE™ 7341 thermal wave tool. Results from this evaluation are presented in Table 4, where and "248 nm $E_0$" is the 248 nanometer exposure dose to clear expressed in millijoules/centimeter$^2$, and "UFTL" is the unexposed film thickness loss, expressed in Angstroms. As can be seen, the UFTL value for comparative Photoresist 3 is significantly elevated compared to values for inventive Photoresists 1 and 2. A larger UFTL value imparts severe top loss (mottling) and reduces the aspect ratio after the development cycle.

TABLE 4

| Photoresist | 248 nm $E_0$ (mJ/cm$^2$) | UFTL (Å) |
|---|---|---|
| 1 | 30.8 | 13.0 |
| 2 | 31.9 | 14.0 |
| 3 (comparative) | 37.5 | 31.0 |

Photoresist compositions containing copolymer 4 and comparative copolymer 7 were each independently formulated as summarized in Table 5. Each component amount in Table 5 is expressed in weight percent based on total solids, excluding solvents. The non-polymeric photoacid generator, ECPPDBT AdOH-TFBS, has the chemical structure

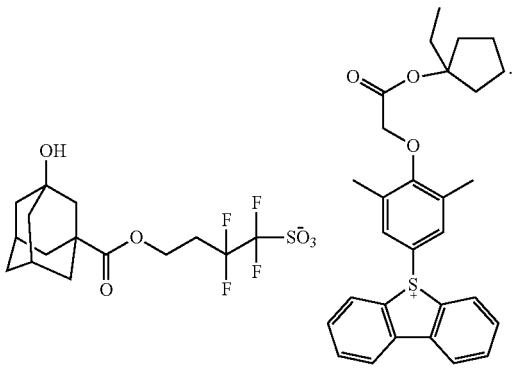

ECPPDBT AdOH-TFBS

The quencher was TIPA, and the surfactant was POLYFOX™ PF-656.

TABLE 5

| Photoresist | Copolymer | PAG | Quencher | Surfactant |
|---|---|---|---|---|
| 4 | 62.4% Copolymer 4 | 35.5% ECPPDBT AdOH-TFBS | 1.5% | 0.1% |
| 5 (comparative) | 62.4% Copolymer 7 | 35.5% ECPPDBT AdOH-TFBS | 1.5% | 0.1% |

All photoresist compositions in Table 5 used a 70:30 (w/w) mixture of ethyl lactate/methyl 2-hydroxyisobutyrate as solvent. The resists were processed at a soft bake of 110° C. for 90 seconds and a post-exposure base at 100° C. for 60 seconds. Contrast curves at 248 nanometers were generated by coating the resist on a 60 nanometer thick organic antireflective layer (Dow Electronic Materials AR™ 9-900). The resist was exposed at 248 nanometers on a Canon TELACT tool. After post-exposure bake, the resists were developed for 60 seconds using 0.26 Normal tetramethylammonium hydroxide solution. Film thickness values were measured using KLA Tencore OPTIPROBE™ 7341 thermal wave tool. Results from this evaluation are presented in Table 6, where "248 nm $E_0$" is the 248 nanometer exposure dose-to-clear expressed in millijoules/centimeter$^2$, and "UFTL" is the unexposed film thickness loss, expressed in Angstroms. As can be seen, the UFTL value for comparative Photoresist 5 is slightly higher compared to that for inventive Photoresist 4.

TABLE 6

| Photoresist | 248 nm $E_0$ (mJ/cm$^2$) | UFTL (Å) |
| --- | --- | --- |
| 4 | 16.0 | 43.0 |
| 5 (comparative) | 14.5 | 47.5 |

Photoresist compositions 1 and 2 were evaluated under extreme ultraviolet (EUV) exposure conditions. Each photoresist composition was passed through a 0.2 micrometer polytetrafluoroethylene filter prior to use. Photoresist compositions were spun cast to a resist thickness of 50 nanometers on eight inch (203.2 millimeter) diameter silicon wafers pre-coated with 25 nanometers of organic antireflective layer (Dow Electronic Materials AR™ 9-900). The films were annealed at 130° C. for 90 seconds, and exposed to EUV light source (NA=0.30; Quad; 0.22σ/0.68σ) using a binary mask containing dark field line/space patterns. The exposed wafers were post-exposure baked at 100° C. for 60 seconds and then developed with 0.26 Normal tetramethylammonium hydroxide solution for 30 seconds.

Photolithographic results are summarized in Table 7, where "$E_{size}$" is sizing energy expressed in units of millijoules per centimeter$^2$, "PCM" is pattern collapse margin expressed in units of nanometers, "LWR" is line width roughness expressed in units of nanometers, and "Exp. Latitude" is the exposure latitude expressed in units of percent. Exposure latitude was defined as a difference in exposure energy to print +/−10% of the target diameter normalized by the sizing energy. The results in Table 7 show that inventive copolymers and corresponding photoresist compositions demonstrate resolution of features as small as 26 nm half pitch (hp) line/space at an acceptable photospeed, good pattern collapse margin and exposure latitude, as well as acceptable LWR.

TABLE 7

| Photoresist | 26 nm hp $E_{size}$ (mJ/cm$^2$) | 26 nm PCM (nm) | 26 nm hp LWR (nm) | 26 nm Exp. Latitude (%) |
| --- | --- | --- | --- | --- |
| 1 | 15.55 | 20.8 | 4.6 | 11.8 |
| 2 | 12.50 | 19.5 | 4.9 | 14.7 |

Photoresist compositions containing copolymer 3 and comparative copolymer 6 were formulated as summarized in Table 8. Component amounts in Table 8 are expressed in weight percent, based on total solids, excluding solvents. The quencher was THIPDA, which has the chemical structure

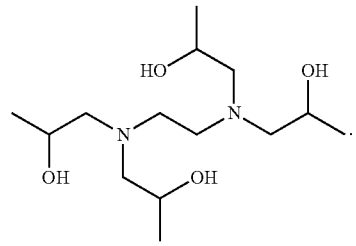 [SMILES: CC(O)CN(CCN(CC(C)O)CC(C)O)CC(C)O]

The surfactant was POLYFOX™ PF-656. These photoresist compositions included no non-polymeric photoacid generator.

TABLE 8

| Photoresist | Copolymer | Quencher | Surfactant |
| --- | --- | --- | --- |
| 6 | 98.6% Copolymer 3 | 1.5% THIPDA | 0.1% |
| 7 (comparative) | 98.6% Copolymer 6 | 1.5% THIPDA | 0.1% |

Photoresist compositions 6 and 7 were evaluated under EUV exposure conditions. Each photoresist composition was passed through a 0.2 micrometer polytetrafluoroethylene filter prior to use. Resist formulations were spun cast to a resist thickness of 30 nanometers on an eight inch (203.2 millimeter) diameter silicon wafers pre-coated with 25 nanometers of a silicon-based antireflective underlayer. The films were annealed at 130° C. for 90 seconds and exposed to an EUV light source (NA=0.30; Quad; 0.22σ/0.68σ using a binary mask containing dark field line/space patterns. The exposed wafers were post-exposure baked at 100° C. for 60 seconds and then developed with 0.26 Normal tetramethylammonium hydroxide solution for 30 seconds.

Photolithographic results are summarized in Table 9, where "$E_{size}$" is sizing energy and "LWR" is line width roughness. Photoresist 6 and comparative Photoresist 7 resolve 22 nm half pitch (hp) line/space features. However, inventive Photoresist 6 exhibited improved photospeed and line width roughness (LWR) relative to comparative Photoresist 7.

TABLE 9

| Photoresist | 22 nm hp $E_{size}$ (mJ/cm$^2$) | 22 nm hp LWR (nm) |
| --- | --- | --- |
| 6 | 21.63 | 4.8 |
| 7 (comparative) | 28.59 | 5.5 |

The invention claimed is:
1. A monomer having the structure

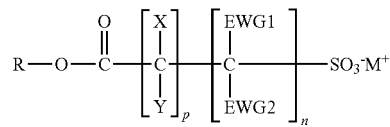

wherein
R is an organic group consisting of (A) a polymerizable carbon-carbon double bond or carbon-carbon triple bond group selected from the group consisting of $C_{2-12}$ alkenyl, $C_{2-12}$ alkynyl, acryloyl, 2-($C_{1-12}$-alkyl) acryloyl, 2-($C_{1-12}$-fluoroalkyl)acryloyl, 2-cyanoacryloyl, and 2-fluoroacryloyl, and (B) one or more divalent groups selected from a straight chain or branched non-fluorinated $C_{1-20}$ alkylene group, a monocyclic or polycyclic non-fluorinated $C_{3-20}$ cycloalkylene group, a monocyclic or polycyclic $C_{3-20}$ heterocycloalkylene group, a monocyclic or polycyclic $C_{6-20}$ arylene group, a monocyclic or polycyclic $C_{1-20}$ heteroarylene group, and a combination thereof;

wherein the $C_{1-20}$ alkylene group, $C_{3-20}$ cycloalkylene group, the monocyclic or polycyclic $C_{3-20}$ heterocycloalkylene group, the monocyclic or polycyclic $C_{6-20}$ arylene group, and the monocyclic or polycyclic $C_{1-20}$ heteroarylene group are optionally substituted with at least one monovalent substituent selected from chlorine, bromine, iodine, hydroxyl, amino, thiol, carboxyl, carboxylate, amide, nitrile, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl;

X and Y are independently at each occurrence hydrogen or a non-fluorinated non-hydrogen substituent;

EWG1 and EWG2 are independently at each occurrence an electron-withdrawing group;

p is 1, 2, 3, or 4;

n is 2, 3, or 4; and $M^+$ is an organic cation.

2. The monomer of claim 1, wherein EWG1 and EWG2 are independently at each occurrence F, partially fluorinated alkyl or perfluorinated alkyl.

3. The monomer of claim 2, wherein EWG1 and EWG2 are at each occurrence F.

4. The monomer of claim 1, wherein EWG1 and EWG2 are independently at each occurrence F, $CF_3$, —CN, —$NO_2$, —C(=O)$R^{11}$, —C(=O)O$R^{11}$, and —$SO_2R^{11}$, wherein $R^{11}$ is a $C_{1-30}$ aliphatic organic group, a $C_{6-30}$ aromatic organic group, or a $C_{1-30}$ heteroaromatic organic group.

5. The monomer of claim 1, wherein R is selected from the group consisting of

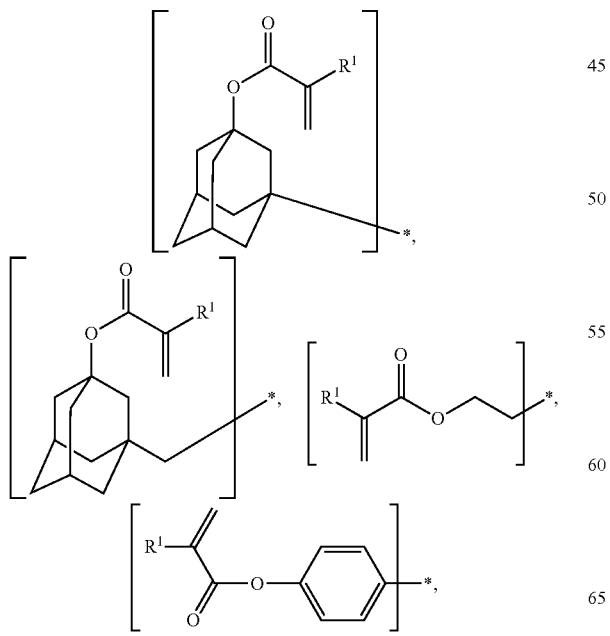

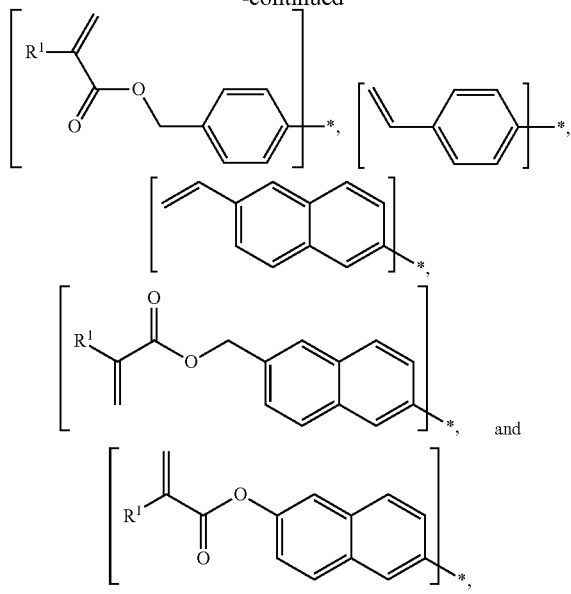

wherein $R^1$ is hydrogen, fluoro, cyano, $C_{1-10}$ alkyl, or $C_{1-10}$ fluoroalkyl.

6. A monomer having the structure

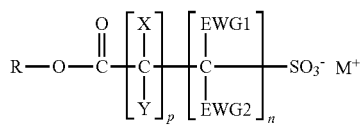

wherein

R is an organic group consisting of (A) a polymerizable carbon-carbon double bond or carbon-carbon triple bond group selected from the group consisting of $C_{2-12}$ alkenyl, $C_{2-12}$ alkynyl, acryloyl, 2-($C_{1-12}$-alkyl)acryloyl, 2-($C_{1-12}$-fluoroalkyl)acryloyl, 2-cyanoacryloyl, and 2-fluoroacryloyl, and (B) one or more divalent groups selected from a straight chain or branched non-fluorinated $C_{1-20}$ alkylene group, a monocyclic or polycyclic non-fluorinated $C_{3-20}$ cycloalkylene group, a monocyclic or polycyclic $C_{3-20}$ heterocycloalkylene group, a monocyclic or polycyclic $C_{6-20}$ arylene group, a monocyclic or polycyclic $C_{1-20}$ heteroarylene group, and a combination thereof;

wherein the $C_{1-20}$ alkylene group, the $C_{3-20}$ cycloalkylene group, the monocyclic or polycyclic $C_{3-20}$ heterocycloalkylene group, the monocyclic or polycyclic $C_{6-20}$ arylene group, and the monocyclic or polycyclic $C_{1-20}$ heteroarylene group are optionally substituted with at least one monovalent substituent selected from chlorine, bromine, iodine, hydroxyl, amino, thiol, carboxyl, carboxylate, amide, nitrile, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl;

X and Y are independently at each occurrence hydrogen or a non-fluorinated non-hydrogen substituent;

EWG1 and EWG2 are independently at each occurrence an electron-withdrawing group;

p is 1, 2, 3, or 4;

n is 1, 2, 3, or 4, provided that the sum of n and p is at least 3; and

M⁺ is an organic cation.

7. A monomer having the structure

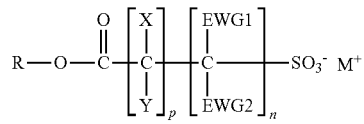

wherein

R is an organic group consisting of (A) a polymerizable carbon-carbon double bond or carbon-carbon triple bond group selected from the group consisting of $C_{2-12}$ alkenyl, $C_{2-12}$ alkynyl, acryloyl, 2-($C_{1-12}$-alkyl)acryloyl, 2-($C_{1-12}$-fluoroalkyl)acryloyl, 2-cyanoacryloyl, and 2-fluoroacryloyl, and (B) one or more divalent groups selected from a straight chain or branched non-fluorinated $C_{1-20}$ alkylene group, a monocyclic or polycyclic non-fluorinated $C_{3-20}$ cycloalkylene group, a monocyclic or polycyclic $C_{3-20}$ heterocycloalkylene group, a monocyclic or polycyclic $C_{6-20}$ arylene group, a monocyclic or polycyclic $C_{1-20}$ heteroarylene group, and any combination thereof;

wherein the $C_{1-20}$ alkylene group, the $C_{3-20}$ cycloalkylene group, the monocyclic or polycyclic $C_{3-20}$ heterocycloalkylene group, the monocyclic or polycyclic $C_{6-20}$ arylene group, and the monocyclic or polycyclic $C_{1-20}$ heteroarylene group are optionally substituted with at least one monovalent substituent selected from chlorine, bromine, iodine, hydroxyl, amino, thiol, carboxyl, carboxylate, amide, nitrile, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl;

EWG1 and EWG2 are independently at each occurrence an electron-withdrawing group;

n is 1, 2, 3, or 4;

p is 1, 2, 3, or 4;

X and Y are hydrogen; and

M⁺ is an organic cation.

8. The monomer of claim 1, selected from the group consisting of

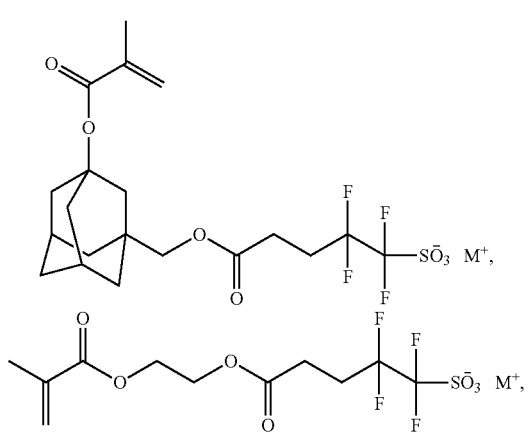

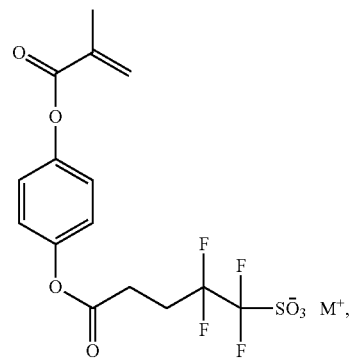

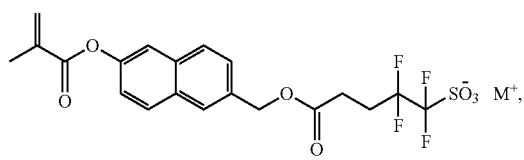

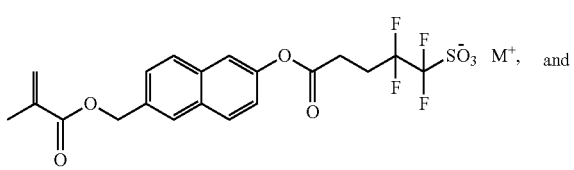

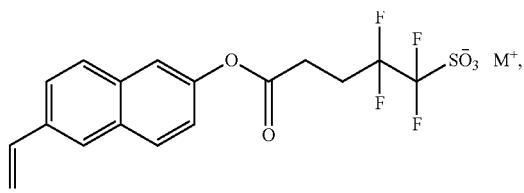

wherein M⁺ is defined as in claim 1.

9. The monomer of claim 1, selected from the group consisting of

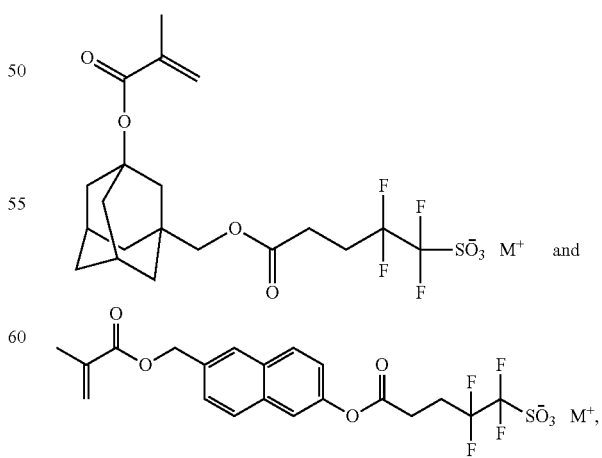

wherein M⁺ is defined as in claim 1.

10. The monomer of claim 1, selected from the group consisting of:

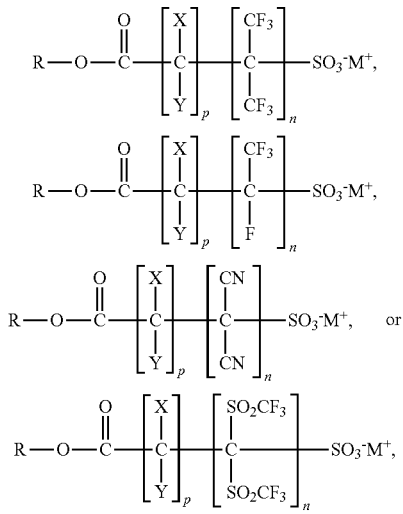

wherein R, X, Y, M, n, and p are as defined in claim 1.

11. The monomer of claim 6, selected from the group consisting of:

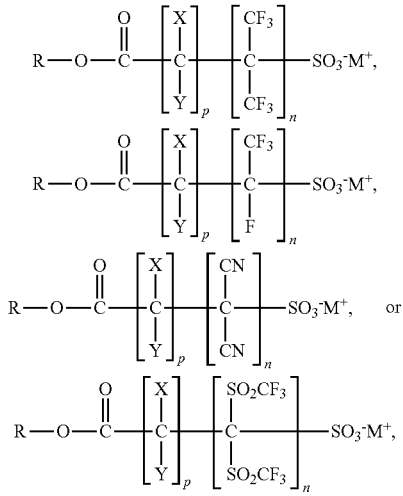

wherein R, X, Y, M, n, and p are as defined in claim 6.

12. The monomer of claim 7, selected from the group consisting of:

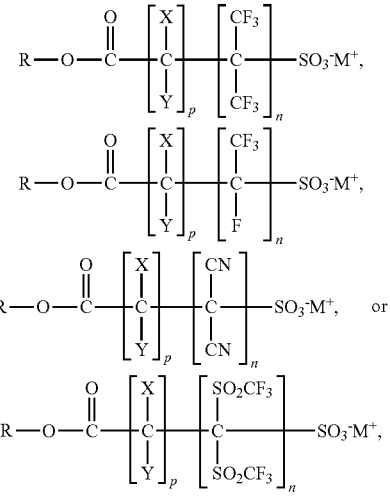

wherein R, X, Y, M, n, and p are as defined in claim 7.

13. The monomer of claim 1, wherein the $C_{1-20}$ alkylene group, $C_{3-20}$ cycloalkylene group, the monocyclic or polycyclic $C_{3-20}$ heterocycloalkylene group, the monocyclic or polycyclic $C_{6-20}$ arylene group, and the monocyclic or polycyclic $C_{1-20}$ heteroarylene group are optionally substituted with at least one monovalent substituent selected from hydroxyl, amino, thiol, carboxyl, carboxylate, amide, nitrile, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl.

14. The monomer of claim 6, wherein the $C_{1-20}$ alkylene group, $C_{3-20}$ cycloalkylene group, the monocyclic or polycyclic $C_{3-20}$ heterocycloalkylene group, the monocyclic or polycyclic $C_{6-20}$ arylene group, and the monocyclic or polycyclic $C_{1-20}$ heteroarylene group are optionally substituted with at least one monovalent substituent selected from hydroxyl, amino, thiol, carboxyl, carboxylate, amide, nitrile, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl.

15. The monomer of claim 7, wherein the $C_{1-20}$ alkylene group, $C_{3-20}$ cycloalkylene group, the monocyclic or polycyclic $C_{3-20}$ heterocycloalkylene group, the monocyclic or polycyclic $C_{6-20}$ arylene group, and the monocyclic or polycyclic $C_{1-20}$ heteroarylene group are optionally substituted with at least one monovalent substituent selected from hydroxyl, amino, thiol, carboxyl, carboxylate, amide, nitrile, nitro, $C_{1-18}$ alkyl, $C_{1-18}$ alkoxyl, $C_{6-18}$ aryl, $C_{6-18}$ aryloxyl, $C_{7-18}$ alkylaryl, or $C_{7-18}$ alkylaryloxyl.

* * * * *